(12) United States Patent
Hastrup et al.

(10) Patent No.: US 6,458,927 B1
(45) Date of Patent: *Oct. 1, 2002

(54) POLYPEPTIDE WITH APPETITE REGULATING ACTIVITY

(75) Inventors: Sven Hastrup, Copenhagen; Kennet Christiansen, Rødovre; Lars Thim, Gentofte; Martin Edward Judge, Copenhagen; Peter Kristensen, Brønshøj, all of (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/048,502

(22) Filed: Mar. 26, 1998

Related U.S. Application Data

(60) Provisional application No. 60/044,188, filed on Apr. 24, 1997, and provisional application No. 60/066,527, filed on Nov. 25, 1997.

(30) Foreign Application Priority Data

Mar. 26, 1997 (DK) ................................................ 0358/97
Nov. 19, 1997 (DK) ................................................ 1315/97

(51) Int. Cl.⁷ ................................................. C07K 1/00
(52) U.S. Cl. ...................... 530/350; 530/350; 530/300; 435/69.1; 435/252.3; 435/320.1; 435/240.1; 435/69.4; 514/12; 536/23.1
(58) Field of Search ............................ 435/252.3, 69.1, 435/320.1, 325, 240.1, 69.4; 536/23.1; 530/350, 300; 514/12

(56) References Cited

U.S. PATENT DOCUMENTS 5,798,258 A * 8/1998 Douglass ................. 435/252.3

FOREIGN PATENT DOCUMENTS

| WO | WO 96/34619 | 11/1996 |
|----|-------------|---------|
| WO | WO 98/48824 | * 11/1998 |

OTHER PUBLICATIONS

Spiess et al., Biochemistry, vol. 20, pp. 1982–1988, 1981.*

Douglas et al., Gene, vol. 169, pp. 241–245, 1996.*

Alignments.*

Kristensen et al., Health Care Discovery, pp. 1–19.

CAPLUS, AN 1996: 173319.

CAPLUS, AN 1995: 451495.

Douglass et al., The Journal of Neuroscience, vol. 15, pp. 2471–2481 (1995).

Douglass et al., Gene, vol. 169, pp. 241–245 (1996).

* cited by examiner

*Primary Examiner*—Karen Cochrane Carlson
*Assistant Examiner*—Hope A. Robinson
(74) *Attorney, Agent, or Firm*—Reza Green, Esq.

(57) ABSTRACT

The present invention relates to a polypeptide with appetite regulating function/activity, a nucleic acid construct encoding the polypeptide and a method of producing the polypeptide. The invention further relates to recombinant vectors comprising the nucleic acid construct encoding the polypeptide, recombinant host cells comprising the nucleic acid construct or the recombinant vector.

14 Claims, 16 Drawing Sheets

Expression in Yeast

Sequence of Heterologous protein expression cassette of plasmid pEA182

```
                                              MetArg PheProSer IlepheThr
1141 CTATCAATTT CATACACAAT ATAAACGATT AAAAGAATGA GATTTCCTTC AATTTTTACT
     GATAGTTAAA GTATGTGTTA TATTTGCTAA TTTTCTTACT CTAAAGGAAG TTAAAAATGA AlaValLeuPhe AlaAlaSer SerAlaLeu AlaAlaProVal AsnThrThr ThrGluAsp
1201 GCAGTTTTAT TCGCAGCATC CTCCGCATTA GCTGCTCCAG TCAACACTAC AACAGAAGAT
     CGTCAAAATA AGCGTCGTAG GAGGCGTAAT CGACGAGGTC AGTTGTGATG TTGTCTTCTA GluThrAlaGln IleProAla GluAlaVal IleGlyTyrser AspLeuGlu GlyAspPhe
1261 GAAACGGCAC AAATTCCGGC TGAAGCTGTC ATCGGTTACT CAGATTTAGA AGGGGATTTC
     CTTTGCCGTG TTTAAGGCCG ACTTCGACAG TAGCCAATGA GTCTAAATCT TCCCCTAAAG AspValAlaVal LeuProPhe SerAsnSer ThrAsnAsnGly LeuLeuPhe IleAsnThr
1321 GATGTTGCTG TTTTGCCATT TTCCAACAGC ACAAATAACG GGTTATTGTT TATAAATACT
     CTACAACGAC AAAACGGTAA AAGGTTGTCG TGTTTATTGC CCAATAACAA ATATTTATGA -NcoI--
     ThrIleAlaSer IleAlaAla LysGluGlu GlyValSerMet AlaLysArg GlnGluAsp
1381 ACTATTGCCA GCATTGCTGC TAAAGAAGAA GGGGTATCCA TGGCTAAGAG ACAGGAGGAT
     TGATAACGGT CGTAACGACG ATTTCTTCTT CCCCATAGGT ACCGATTCTC TGTCCTCCTA AlaGluLeuGln ProArgAla LeuAspIle TySerAlaVal AspAspAla SerHisGlu
1441 GCCGAGCTGC AGCCCCGAGC CCTGGACATC TACTCTGCCG TGGATGATGC GTCCCATGAG
     CGGCTCGACG TCGGGGCTCG GGACCTGTAG ATGAGACGGC ACCTACTACG CAGGGTACTC LysGluLeuIle GluAlaLeu GlnGluVal LeuLysLysLeu LysSerLys ArgIlePro
1501 AAGGAGCTGA TTGAAGCGCT GCAGGAAGTC CTGAAGAAGC TCAAGAGTAA ACGCATTCCG
     TTCCTCGACT AACTTCGCGA CGTCCTTCAG GACTTCTTCG AGTTCTCATT TGCGTAAGGC IleTyrGluLys LysTyrGly GlnValPro MetCysAspAla GlyGluGln CysAlaVal
1561 ATCTATGAGA AGAAGTACGG CCAAGTCCCC ATGTGTGACG CTGGAGAGCA GTGCGCAGTG
     TAGATACTCT TCTTCATGCC GGTTCAGGGG TACACACTGC GACCTCTCGT CACGCGTCAC ArgLysGlyAla ArgIleGly LysLeuCys AspCysProArg GlyThrSer CysAsnSer
1621 CGGAAAGGGG CCAGGATCGG GAAGCTGTGT GACTGTCCCC GAGGAACTTC TTGCAATTCT
     GCCTTTCCCC GGTCCTAGCC CTTCGACACA CTGACAGGGG CTCCTTGAAG AACGTTAAGA -XbaI--
     PheLeuLeuLys CysLeu
1681 TTCCTCTTGA AGTGCTTGTG ATCTAGAAAC TAAGATTAAT ATAATTATAT AAAAATATTA
     AAGGAGAACT TCACGAACAC TAGATCTTTG ATTCTAATTA TATTAATATA TTTTTATAAT
```

FIG 5A

Sequence of Heterologous protein expression cassette of plasmid pEA182

```
                                           MetArg PheProSer IlepheThr
1141  CTATCAATTT CATACACAAT ATAAACGATT AAAAGAATGA GATTTCCTTC AATTTTTACT
      GATAGTTAAA GTATGTGTTA TATTTGCTAA TTTTCTTACT CTAAAGGAAG TTAAAAATGA AlaValLeuPhe AlaAlaSer SerAlaLeu AlaAlaProVal AsnThrThr ThrGluAsp
1201  GCAGTTTTAT TCGCAGCATC CTCCGCATTA GCTGCTCCAG TCAACACTAC AACAGAAGAT
      CGTCAAAATA AGCGTCGTAG GAGGCGTAAT CGACGAGGTC AGTTGTGATG TTGTCTTCTA GluThrAlaGln IleProAla GluAlaVal IleGlyTyrser AspLeuGlu GlyAspPhe
1261  GAAACGGCAC AAATTCCGGC TGAAGCTGTC ATCGGTTACT CAGATTTAGA AGGGGATTTC
      CTTTGCCGTG TTTAAGGCCG ACTTCGACAG TAGCCAATGA GTCTAAATCT TCCCCTAAAG AspValAlaVal LeuProPhe SerAsnSer ThrAsnAsnGly LeuLeuPhe IleAsnThr
1321  GATGTTGCTG TTTTGCCATT TTCCAACAGC ACAAATAACG GGTTATTGTT TATAAATACT
      CTACAACGAC AAAACGGTAA AAGGTTGTCG TGTTTATTGC CCAATAACAA ATATTTATGA
                                                                 -NcoI--
         ThrIleAlaSer IleAlaAla LysGluGlu GlyValSerMet AlaLysArg GlnGluAsp
1381  ACTATTGCCA GCATTGCTGC TAAAGAAGAA GGGGTATCCA TGGCTAAGAG ACAGGAGGAT
      TGATAACGGT CGTAACGACG ATTTCTTCTT CCCCATAGGT ACCGATTCTC TGTCCTCCTA AlaGluLeuGln ProArgAla LeuAspIle TySerAlaVal AspAspAla SerHisGlu
1441  GCCGAGCTGC AGCCCCGAGC CCTGGACATC TACTCTGCCG TGGATGATGC GTCCCATGAG
      CGGCTCGACG TCGGGGCTCG GGACCTGTAG ATGAGACGGC ACCTACTACG CAGGGTACTC LysGluLeuPro ArgArgGln LeuArgAla ProGlyAlaVal LeuGlnIle GluAlaLeu
1501  AAGGAGCTGC CAAGGCGGCA ACTTCGGGCT CCCGGCGCTG TGTTGCAGAT TGAAGCGCTG
      TTCCTCGACG GTTCCGCCGT TGAAGCCCGA GGGCCGCGAC ACAACGTCTA ACTTCGCGAC GlnGluValLeu LysLysLeu LysSerLys ArgIleProIle TyrGluLys LysTyrGly
1561  CAGGAAGTCC TGAAGAAGCT CAAGAGTAAA CGCATTCCGA TCTATGAGAA GAAGTACGGC
      GTCCTTCAGG ACTTCTTCGA GTTCTCATTT GCGTAAGGCT AGATACTCTT CTTCATGCCG GlnValProMet CysAspAla GlyGluGln CysAlaValArg LysGlyAla ArgIleGly
1621  CAAGTCCCCA TGTGTGACGC TGGAGAGCAG TGCGCAGTGC GGAAAGGGGC CAGGATCGGG
      GTTCAGGGGT ACACACTGCG ACCTCTCGTC ACGCGTCACG CCTTTCCCCG GTCCTAGCCC LysLeuCysAsp CysProArg GlyThrSer CysAsnSerPhe LeuLeuLys CysLeu
1681  AAGCTGTGTG ACTGTCCCCG AGGAACTTCT TGCAATTCTT TCCTCTTGAA GTGCTTGTGA
      TTCGACACAC TGACAGGGGC TCCTTGAAGA ACGTTAAGAA AGGAGAACTT CACGAACACT
      -XbaI--
1741  TCTAGAAACT AAGATTAATA TAATTATATA AAAATATTAT CTTCTTTTCT TTATATCTAG
      AGATCTTTGA TTCTAATTAT ATTAATATAT TTTTATAATA GAAGAAAAGA AATATAGATC
```

FIG 5B

Primary and secondary structure of "IPI-CART" showing the I-III, II-V and IV-VI disulphide bond configuration.

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 102 amino acids
      (B) TYPE: amino acid
      (D) TOPOLOGY: linear (ii) MOLECULE TYPE: peptide (xi) SEQUENCE DESCRIPTION: SEQ ID NO: 1:

```
Gln Glu Asp Ala Glu Leu Gln Pro Arg Ala Leu Asp Ile Tyr Ser Ala
1               5                   10                  15

Val Asp Asp Ala Ser His Glu Lys Glu Leu Pro Arg Arg Gln Leu Arg
                20                  25                  30

Ala Pro Gly Ala Val Leu Gln Ile Glu Ala Leu Gln Glu Val Leu Lys
            35                  40                  45

Lys Leu Lys Ser Lys Arg Ile Pro Ile Tyr Glu Lys Lys Tyr Gly Gln
    50                  55                  60

Val Pro Met Cys Asp Ala Gly Glu Gln Cys Ala Val Arg Lys Gly Ala
65                  70                  75                  80

Arg Ile Gly Lys Leu Cys Asp Cys Pro Arg Gly Thr Ser Cys Asn Ser
                85                  90                  95

Phe Leu Leu Lys Cys Leu
            100
```

(2) INFORMATION FOR SEQ ID NO: 2:

(i) SEQUENCE CHARACTERISTICS:

(A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO: 2:

Gln Glu Asp Ala Glu Leu Gln Pro Arg Ala Leu Asp Ile Tyr Ser Ala
1               5                   10                  15

Val Asp Asp Ala Ser His Glu Lys Glu Leu Ile Glu Ala Leu Gln Glu
                20                  25                  30

Val Leu Lys Lys Leu Lys Ser Lys Arg Ile Pro Ile Tyr Glu Lys Lys
                35                  40                  45

Tyr Gly Gln Val Pro Met Cys Asp Ala Gly Glu Gln Cys Ala Val Arg
            50                  55                  60

Lys Gly Ala Arg Ile Gly Lys Leu Cys Asp Cys Pro Arg Gly Thr Ser
65                  70                  75                  80

Cys Asn Ser Phe Leu Leu Lys Cys Leu
                85

(2) INFORMATION FOR SEQ ID NO: 3:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO: 3:

Gln Glu Asp Ala Glu Leu Gln Pro Arg Ala Leu Asp Ile Tyr Ser Ala
1               5                   10                  15

Val Asp Asp Ala Ser His Glu Lys Glu Leu Ile Glu Ala Leu Gln Glu
                20                  25                  30

Val Leu Lys Lys Leu Lys Ser Lys Arg Val Pro Ile Tyr Glu Lys Lys
                35                  40                  45

Tyr Gly Gln Val Pro Met Cys Asp Ala Gly Glu Gln Cys Ala Val Arg
            50                  55                  60

Lys Gly Ala Arg Ile Gly Lys Leu Cys Asp Cys Pro Arg Gly Thr Ser
65                  70                  75                  80

Cys Asn Ser Phe Leu Leu Lys Cys Leu
                85

(2) INFORMATION FOR SEQ ID NO: 4:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO: 4:

Ile Pro Ile Tyr Glu Lys Lys Tyr Gly Gln Val Pro Met Cys Asp Ala
1               5                   10                  15

Gly Glu Gln Cys Ala Val Arg Lys Gly Ala Arg Ile Gly Lys Leu Cys
                20                  25                  30

Asp Cys Pro Arg Gly Thr Ser Cys Asn Ser Phe Leu Leu Lys Cys Leu
            35                  40                  45

(2) INFORMATION FOR SEQ ID NO: 5:

(i) SEQUENCE CHARACTERISTICS:
    (A) LENGTH: 48 amino acids
    (B) TYPE: amino acid
    (D) TOPOLOGY: linear (ii) MOLECULE TYPE: protein (xi) SEQUENCE DESCRIPTION: SEQ ID NO: 5:

```
Val Pro Ile Tyr Glu Lys Lys Tyr Gly Gln Val Pro Met Cys Asp Ala
1               5                   10                  15
Gly Glu Gln Cys Ala Val Arg Lys Gly Ala Arg Ile Gly Lys Leu Cys
            20                  25                  30
Asp Cys Pro Arg Gly Thr Ser Cys Asn Ser Phe Leu Leu Lys Cys Leu
        35                  40                  45
```

(2) INFORMATION FOR SEQ ID NO: 6:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO: 6:

```
Arg Ile Pro Ile Tyr Glu Lys Lys Tyr Gly Gln Val Pro Met Cys Asp
1               5                   10                  15
Ala Gly Glu Gln Cys Ala Val Arg Lys Gly Ala Arg Ile Gly Lys Leu
            20                  25                  30
Cys Asp Cys Pro Arg Gly Thr Ser Cys Asn Ser Phe Leu Leu Lys Cys
        35                  40                  45
Leu
```

(2) INFORMATION FOR SEQ ID NO: 7:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (xi) SEQUENCE DESCRIPTION: SEQ ID NO: 7:

```
Lys Tyr Gly Gln Val Pro Met Cys Asp Ala Gly Glu Gln Cys Ala Val
1               5                   10                  15
Arg Lys Gly Ala Arg Ile Gly Lys Leu Cys Asp Cys Pro Arg Gly Thr
            20                  25                  30
Ser Cys Asn Ser Phe Leu Leu Lys Cys Leu
        35                  40
```

(2) INFORMATION FOR SEQ ID NO: 8:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 8:

```
Tyr Gly Gln Val Pro Met Cys Asp Ala Gly Glu Gln Cys Ala Val Arg
1               5                   10                  15
Lys Gly Ala Arg Ile Gly Lys Leu Cys Asp Cys Pro Arg Gly Thr Ser
```

-continued

```
                  20                  25                  30

Cys Asn Ser Phe Leu Leu Lys Cys Leu
         35                  40
```

(2) INFORMATION FOR SEQ ID NO: 9:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO: 9:

```
Cys Asp Ala Gly Glu Gln Cys Ala Val Arg Lys Gly Ala Arg Ile Gly
1               5                   10                  15

Lys Leu Cys Asp Cys Pro Arg Gly Thr Ser Cys Asn Ser Phe Leu Leu
                20                  25                  30

Lys Cys Leu
         35
```

(2) INFORMATION FOR SEQ ID NO: 10:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 10:

```
Ala Leu Asp Ile Tyr Ser Ala Val Asp Asp Ala Ser His Glu Lys Glu
1               5                   10                  15

Leu Ile Glu Ala Leu Gln Glu Val Leu Lys Lys Leu Lys Ser Lys Arg
                20                  25                  30

Ile Pro Ile Tyr Glu Lys Lys Tyr Gly Gln Val Pro Met Cys Asp Ala
                35                  40                  45

Gly Glu Gln Cys Ala Val Arg Lys Gly Ala Arg Ile Gly Lys Leu Cys
         50                  55                  60

Asp Cys Pro Arg Gly Thr Ser Cys Asn Ser Phe Leu Leu Lys Cys Leu
65                  70                  75                  80
```

(2) INFORMATION FOR SEQ ID NO: 11:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 11:

```
Ala Leu Asp Ile Tyr Ser Ala Val Asp Asp Ala Ser His Glu Lys Glu
1               5                   10                  15

Leu Ile Glu Ala Leu Gln Glu Val Leu Lys Lys Leu Lys Ser Lys Arg
                20                  25                  30

Val Pro Ile Tyr Glu Lys Lys Tyr Gly Gln Val Pro Met Cys Asp Ala
```

-continued

```
                    35                  40                  45
Gly Glu Gln Cys Ala Val Arg Lys Gly Ala Arg Ile Gly Lys Leu Cys
        50                  55                  60

Asp Cys Pro Arg Gly Thr Ser Cys Asn Ser Phe Leu Leu Lys Cys Leu
65                  70                  75                  80
```

POLYPEPTIDE WITH APPETITE REGULATING ACTIVITY

CROSS REFERENCE TO RELATED APPLICATIONS

This application claims priority of Provisional application Ser. Nos. 60/044,188 and 60/066,527 filed Apr. 24, 1997 and Nov. 25, 1997, and Danish applications serial nos. 0358/97 and 1315/97 filed on Mar. 26, 1997 and Nov. 19, 1997, respectively, the contents of which are fully incorporated herein by reference.

FIELD OF INVENTION

The present invention relates to a polypeptide with appetite regulating function/activity, a nucleic acid construct encoding the polypeptide and a method of producing the polypeptide. The invention further relates to recombinant vectors comprising the nucleic acid construct encoding the polypeptide, recombinant host cells comprising the nucleic acid construct or the recombinant vector, a transgenic animal or plant containing and expressing the nucleic acid construct, an appetite regulating composition comprising the polypeptide, and the use of the polypeptide for regulating appetite.

The polypeptide has appetite regulating activity/function in mammals, including humans.

BACKGROUND OF THE INVENTION

It has been known that certain tumors when implanted into rats after a period of growth suddenly induce severe anorexia and adipsia (lack of eating and drinking) in the animal, whereas closely related tumor lines do not, Madsen et al., *Scand. J. Clin. Invest.* Supplement 220: 27–36.

The aim of this invention has been to find the factor(s) responsible for this characteristic phenotype.

Cocaine and Amphetamine Regulated Transcript (CART) was detected as one of several compounds that was selectively expressed in anorectic versus non-anorectic secondary cultures of glucagonomas. In situ hybridisation analysis of CART mRNA expression has shown a decreased level of CART mRNA in the nucleus arcuatus and nucleus paraventricularis of the rat hypothalamus following fasting. Similarly, CART mRNA in the arcuate nucleus of Zucker rats (fa/fa) was strongly decreased when compared to heterozygote controls (fa/+) as measured by in situ hybridisation. Thus, CART mRNA in the arcuate nucleus demonstrates a pattern of change inverse to that known for NPY. The latter finding provides a strong linkage between the expression of CART and biological factors involved in food intake.

A polypeptide of at least 30 amino acids was found by Spiess et al., 1981, *Biochemistry* 20: 1982–1988 as an HPLC peak when purifying somatostatine from sheep hypothalamus. The isolated polypeptide was the C-terminal (IPI-CART) portion of CART. However, no biological function was associated with this molecule.

The mature CART peptide has so far not been isolated and characterised. A transcript to be upregulated in rat brain after treatment with cocaine and amphetamine relating to CART was cloned. This cloning indicates that the peptide may exist in a long form consisting of 102 amino acid residues or in a short form consisting of 89 amino acid residues (Douglass, J. et al. *J. Neurosci.* 15, 2471–2481, 1995).

The same group found the human gene and cDNA for CART. Only the short form exists in humans (Douglass and Daoud (1996), *Gene* 169: 241–245).

In 1995 Amgen disclosed methods of reducing or preventing neuron degeneration and promoting regeneration and restoration of function induced by CART (WO 96/34619).

SUMMARY OF THE INVENTION

The aim of this invention has been to find the factor(s) responsible for the above described characteristic phenotype.

It has now been found that a polypeptide with the sequence SEQ ID No. 1 and fragments thereof have appetite regulating activity/function:

Gln-Glu-Asp-Ala-Glu-Leu-Gln-Pro-Arg-Ala-Leu-Asp-Ile-Tyr-Ser-Ala-Val-Asp- Asp-Ala-Ser-His-Glu-Lys-Glu-Leu-Pro-Arg-Arg-Gln-Leu-Arg-Ala-Pro-GlY-Ala - Val -Leu-Gln-Ile-Glu-Ala-Leu-Gln-Glu-Val-Leu-Lys-Lys-Leu-Lys-Ser-<u>Lys-Arg</u>- Ile-Pro-Ile-Tyr-Glu-Lys-Lys-Tyr-Gly-Gln-Val-Pro-Met-Cys-Asp-Ala-Gly-Glu- Gln-Cys-Ala-Val-Arg-Lys-Gly-Ala-Arg-Ile-Gly-Lys-Leu-Cys-Asp-Cys-Pro-Arg-Gly-Thr-Ser-Cys-Asn-Ser-Phe-Leu-Leu-Lys-Cys-Leu

Furthermore, it has been found that the following polypeptides have appetite regulating activity/function:

SEQ ID No. 2:
Gln-Glu-Asp-Ala-Glu-Leu-Gln-Pro-Arg-Ala-Leu-Asp-Ile-Tyr-Ser-Ala-Val-Asp- Asp-Ala-Ser-His-Glu-Lys-Glu-Leu-Ile-Glu-Ala-Leu-Gln-Glu-Val-Leu-Lys-Lys- Leu-Lys-Ser-<u>Lys-Arg</u>-Ile-Pro-Ile-Tyr-Glu-Lys-Lys-Tyr-Gly-Gln-Val-Pro-Met- Cys-Asp-Ala-Gly-Glu-Gln-Cys-Ala-Val-Arg-Lys-Gly-Ala-Arg-Ile-Gly-Lys-Leu- Cys-Asp-Cys-Pro-Arg-Gly-Thr-Ser-Cys-Asn-Ser-Phe-Leu-Leu-Lys-Cys-Leu

SEQ ID No. 3:
Gln-Glu-Asp-Ala-Glu-Leu-Gln-Pro-Arg-Ala-Leu-Asp-Ile-Tyr-Ser-Ala-Val-Asp- Asp-Ala-Ser-His-Glu-Lys-Glu-Leu-Ile-Glu-Ala-Leu-Gln-Glu-Val-Leu-Lys-Lys- Leu-Lys-Ser-<u>Lys-Arg</u>-Val-Pro-Ile-Tyr-Glu-Lys-Lys-Tyr-Gly-Gln-Val-Pro-Met- Cys-Asp-Ala-Gly-Glu-Gln-Cys-Ala-Val-Arg-Lys-Gly-Ala-Arg-Ile-Gly-Lys-Leu- Cys-Asp-Cys-Pro-Arg-Gly-Thr-Ser-Cys-Asn-Ser-Phe-Leu-Leu-Lys-Cys-Leu

SEQ ID No. 4:
Ile-Pro-Ile-Tyr-Glu-Lys-Lys-Tyr-Gly-Gln-Val-Pro-Met-Cys-Asp-Ala-Gly-Glu- Gln-Cys-Ala-Val-Arg-Lys-Gly-Ala-Arg-Ile-Gly-Lys-Leu-Cys-Asp-Cys-Pro-Arg- Gly-Thr-Ser-Cys-Asn-Ser-Phe-Leu-Leu-Lys-Cys-Leu

SEQ ID No. 5:
Val-Pro-Ile-Tyr-Glu-Lys-Lys-Tyr-Gly-Gln-Val-Pro-Met-Cys-Asp-Ala-Gly-Glu- Gln-Cys-Ala-Val-Arg-Lys-Gly-Ala-Arg-Ile-Gly-Lys-Leu-Cys-Asp-Cys-Pro-Arg- Gly-Thr-Ser-Cys-Asn-Ser-Phe-Leu-Leu-Lys-Cys-Leu

SEQ ID No. 6:
Arg-Ile-Pro-Ile-Tyr-Glu-Lys-Lys-Tyr-Gly-Gln-Val-Pro-Met-Cys-Asp-Ala-Gly- Glu-Gln-Cys-Ala-Val-Arg-Lys-Gly-Ala-Arg-Ile-Gly-Lys-Leu-Cys-Asp-Cys-Pro- Arg-Gly-Thr-Ser-Cys-Asn-Ser-Phe-Leu-Leu-Lys-Cys-Leu

SEQ ID No. 7:
Lys-Tyr-Gly-Gln-Val-Pro-Met-Cys-Asp-Ala-Gly-Glu-Gln-Cys-Ala-Val-Arg-Lys- Gly-Ala-Arg-Ile-Gly-Lys-Leu-Cys-Asp-Cys-Pro-Arg-Gly-Thr-Ser-Cys-Asn-Ser- Phe-Leu-Leu-Lys-Cys-Leu

SEQ ID No. 8:
Tyr-Gly-Gln-Val-Pro-Met-Cys-Asp-Ala-Gly-Glu-Gln-Cys-Ala-Val-Arg-Lys-Gly- Ala-Arg-Ile-Gly-Lys-Leu-Cys-Asp-Cys-Pro-Arg-Gly-Thr-Ser-Cys-Asn-Ser-Phe- Leu-Leu-Lys-Cys-Leu

SEQ ID No. 9:
Cys-Asp-Ala-Gly-Glu-Gln-Cys-Ala-Val-Arg-Lys-Gly-Ala-Arg-Ile-Gly-Lys-Leu- Cys-Asp-Cys-Pro-Arg-Gly-Thr-Ser-Cys-Asn-Ser-Phe-Leu-Leu-Lys-Cys-Leu

SEQ ID No. 10:
Ala-Leu-Asp-Ile-Tyr-Ser-Ala-Val-Asp-Asp-Ala-Ser-His-Glu-Lys-Glu-Leu-Ile- Glu-Ala-Leu-Gln-Glu-Val-Leu-Lys-Lys-Leu-Lys-Ser-Lys-Arg-Ile-Pro-Ile-Tyr- Glu-Lys-Lys-Tyr-Gly-Gln-Val-Pro-Met-Cys-Asp-Ala-Gly-Glu-Gln-Cys-Ala-Val- Arg-Lys-Gly-Ala-Arg-Ile-Gly-Lys-Leu-Cys-Asp-Cys-Pro-Arg-Gly-Thr-Ser-Cys- Asn-Ser-Phe-Leu-Leu-Lys-Cys-Leu

SEQ ID No.11:
Ala-Leu-Asp-Ile-Tyr-Ser-Ala-Val-Asp-Asp-Ala-Ser-His-Glu-Lys-Glu-Leu-Ile- Glu-Ala-Leu-Gln-Glu-Val-Leu-Lys-Lys-Leu-Lys-Ser-Lys-Arg-Val-Pro-Ile-Tyr- Glu-Lys-Lys-Tyr-Gly-Gln-Val-Pro-Met-Cys-Asp-Ala-Gly-Glu-Gln-Cys-Ala-Val- Arg-Lys-Gly-Ala-Arg-Ile-Gly-Lys-Leu-Cys-Asp-Cys-Pro-Arg-Gly-Thr-Ser-Cys- Asn-Ser-Phe-Leu-Leu-Lys-Cys-Leu

The peptides SEQ ID Nos. 5 to 11 are considered to be novel per se and are constituting a part of the invention.

In a preferred embodiment of the present invention the cysteine residues of the above peptides SEQ ID Nos. 1 to 11 are linked by disulphide bonds in the configuration I–III, II–V and IV–VI when the cysteines are numbered from the N-terminal. These peptides are also considered to be novel per se and are constituting a part of the invention.

In the present context, the term "appetite regulating activity/function" is intended to mean any activity/function which suppresses appetite e.g. by inducing a feeling of satiety or by inhibiting the sensation of hunger. The appetite regulating activity/function may be measured according to the test methods described in Example 9 or 20

In another aspect, the invention relates to nucleic acid constructs comprising a nucleotide sequence encoding a CART polypeptide or a fragment or variant thereof with appetite regulating activity/function.

In a further aspect, the invention relates to nucleic acid constructs encoding a polypeptide with a sequence selected from the sequences SEQ ID Nos. 1 to 9 such as the sequences SEQ ID Nos. 1 to 9 in which the cysteine residues are linked by disulphide bonds in the configuration I–III, II–V and IV–VI when the cysteines are numbered from the N-terminal end.

In a further aspect, the invention relates to recombinant vectors comprising the nucleic acid constructs and recombinant host cells comprising the nucleic acid constructs or the vectors.

In a further aspect, the invention relates to a method of producing a CART polypeptide or a fragment or a variant thereof with appetite regulating activity/function which method comprises cultivating a host cell as defined above in a suitable culture medium under conditions permitting expression of the nucleic acid construct and recovering the resulting polypeptide from the culture medium/cell.

In a further aspect, the invention relates to transgenic animals or transgenic plants comprising the nucleic acid construct as defined above as well as methods of producing a CART polypeptide or a fragment or a variant thereof with appetite regulating activity/function using such transgenic animals or transgenic plants.

In still a further aspect, the invention relates to an antibody capable of specifically binding to a CART polypeptide or a fragment or a variant thereof with appetite regulating activity/function, such as a polypeptide with a sequence selected from the sequences SEQ ID Nos. 1 to 9, e.g. the sequences SEQ ID Nos. 1 to 9 in which the cysteine residues are linked by disulphide bonds in the configuration I–III, II–V and IV–VI when the cysteines are numbered from the N-terminal end. In a preferred embodiment of the invention the antibody is monoclonal and the invention furthermore relates to hybridomas producing such monoclonal antibodies.

In a further aspect, the invention relates to appetite regulating compositions comprising the polypeptides as defined above and a pharmaceutically acceptable carrier and the use of the polypeptides for the preparation of medicaments for the regulation of appetite. In a preferred embodiment of the invention the medicaments are used for the treatment of obesity.

Furthermore, the invention relates to a method for the regulation of appetite comprising administering to a subject in need thereof an effective amount of a polypeptide as defined above. In a further aspect, the invention relates to the use of CART or CART fragments or variants to identify a functional receptor and the subsequent use of the CART receptor to identify receptor agonists with appetite regulating activity.

In a further aspect, the invention relates to compounds that upregulate the CART expression and thereby regulate appetite.

BRIEF DESCRIPTION OF THE DRAWINGS

FIG. 5: Sequence of heterologous protein expression cassette of plasmid pEA182 and pEA183 in yeast.

DETAILED DESCRIPTION OF THE INVENTION

Figure 1:
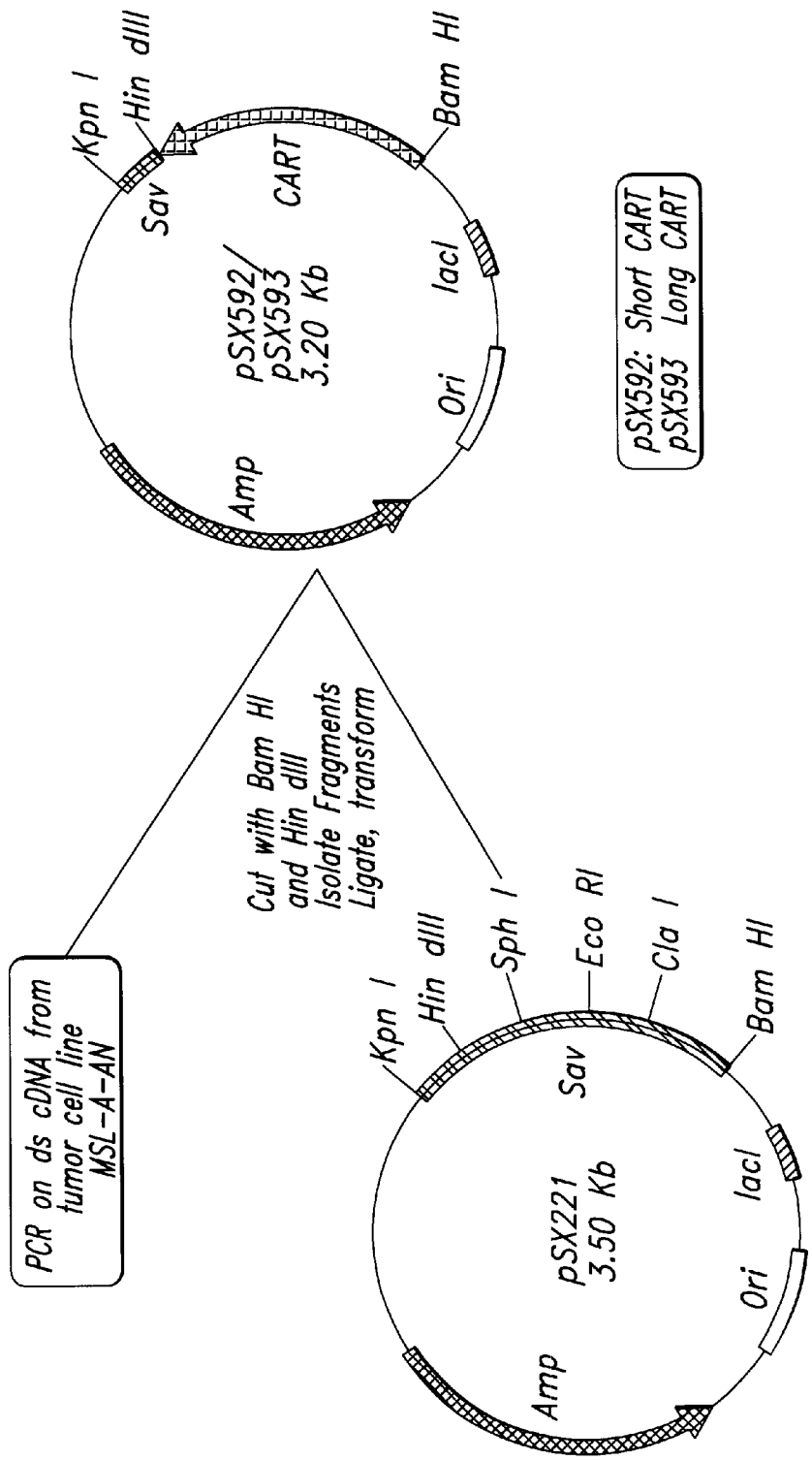
FIG. 1: Cloning of CART.

This invention is based on the unexpected and surprising discovery that CART polypeptide has been found to possess appetite regulating function/activity. In the present context the term "polypeptide" is understood to include a mature protein or a precursor form thereof as well as a functional fragment thereof which essentially has the activity of the full-length polypeptide.

Furthermore, the term "polypeptide" is intended to include homologues of said polypeptide. Such homologues comprise an amino acid sequence exhibiting a degree of identity of at least 60%, preferably 80% with the amino acid sequences shown in SEQ ID Nos. 1–9. The degree of identity may be determined by conventional methods, see for instance, Altshul et al., *Bull. Math. Bio.* 48: 603–616, 1986, and Henikoff and Henikoff, *Proc. Natl. Acad. Sci. U.S. Pat. No.* 89: 10915–10919, 1992. Briefly, two amino acid sequences are aligned to optimize the alignment scores using a gap opening penalty of 10, a gap extension penalty of 1, and the "blosum 62" scoring matrix of Henikoff and Henikoff, supra. Alternatively, the homologue of the polypeptide may be one encoded by a nucleotide sequence hybridizing with an oligonucleotide probe prepared on the basis of the polypeptide sequences shown in SEQ ID Nos. 1–9.

In a further aspect the invention relates to a variant of the polypeptide of the invention. The variant is one in which one or more amino acid residues in one or more positions have been substituted by other amino acid residues.

Homologues of the present polypeptide may have one or more amino acid substitutions, deletions or additions. These changes are preferably of a minor nature, that is conservative amino acid substitutions that do not significantly affect the folding or activity of the protein, small deletions, typically of one to about 30 amino acids, small amino- or carboyxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active polypeptide. Amino acids essential to the activity of the polypeptide of the invention, and therefore preferably not subject to substitution, may be identified according to procedures known in the art, such as site-directed mutagenesis or alanine-scanning mutagenesis (Cunningham and Wells, *Science* 244, 1081–1085, 1989). In the latter technique mutations are introduced at every residue in the molecule, and the resultant mutant molecules are tested for biological activity (e.g. appetite regulation) to identify amino acid residues that are critical to the activity of the molecule. Sites of ligand-receptor interaction can also be determined by analysis of crystal structure as determined by such techniques as nuclear magnetic resonance, crystallography or photoaffinity labelling. See, for example, de Vos et al., *Science* 255: 306–312, 1992; Smith et al., *J. Mol. Biol.* 224: 899–904, 1992; Wlodaver et al., *FEBS Lett.* 309: 59–64, 1992.

The homologue may be an allelic variant, i.e. an alternative form of a gene that arises through mutation, or an altered polypeptide encoded by the mutated gene, but having substantially the same activity as the polypeptide of the invention. Hence mutations can be silent (no change in the encoded polypeptide) or may encode polypeptides having altered amino acid sequence.

The homologue of the present polypeptide may also be a species homologue, i.e. a polypeptide with a similar activity derived from another mammalian species eg. rat, mouse, sheep or human.

Furthermore, homologues of said polypeptide may be found in other tissues such as the brain and pancreas.

A homologue of the polypeptide may be isolated by preparing a genomic or cDNA library of a cell of the species or tissue in question, and screening for DNA sequences coding for all or part of the homologue by using synthetic oligonucleotide probes in accordance with standard techniques, e.g. as described by Sambrook et al., *Molecular Cloning:A Laboratory Manual,* 2nd. Ed. Cold Spring Harbor Laboratory, Cold Spring Harbor, N.Y., 1989, or by means of polymerase chain reaction (PCR) using specific primers as described by Sambrook et al. and Saiki at al., *Science* 239 (1988) 487–491.

It may be preferred to provide the polypeptide in a highly purified form, i.e. greater than 90% pure, more preferably 95% and most preferably 99% pure, as determined by analytical HPLC.

The currently preferred polypeptides of the invention are the ones comprising the amino acid sequences shown in SEQ ID Nos. 1–9.

Nucleic Acid Construct

As used herein the term "nucleic acid construct" is intended to indicate any nucleic acid molecule of cDNA, genomic DNA, synthetic DNA or RNA origin. The term "construct" is intended to indicate a nucleic acid segment which may be single or double stranded, and which may be based on a complete or partial naturally occurring nucleotide sequence encoding a polypeptide of interest. The construct may optionally contain other nucleic acid segments.

The nucleic acid construct of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra). For the present purpose, the DNA sequence encoding the polypeptide is preferably of mammalian origin, i.e. derived from a genomic DNA or cDNA library. More preferably, the DNA sequence may be of rodent origin, e.g. rat or mice origin. Even more preferably, the DNA sequence may be of human origin.

The nucleic acid construct of the invention encoding the polypeptide may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. According to the phospho-amidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or Saiki et al., *Science* 239 (1988), 487–491.

As template for the PCR cloning we used the same double stranded cDNA preparation as described in example 1 (from MSL-A-AN).

The PCR reaction, 25 cycles:

60 sec 94° C.

30 sec 52° C.

60 sec 72° C.

The nucleic acid construct is preferably a DNA construct which term will be used exclusively in the following.

Recombinant Vector

In a further aspect, the present invention relates to a recombinant vector comprising a DNA construct of the invention. The recombinant vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the polypeptide of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

The promoter may be any DNA sequence which shows transcriptional activity in the host cell of choice and may be derived from genes encoding proteins either homologous or heterologous to the host cell.

Examples of suitable promoters for directing the transcription of the DNA encoding the polypeptide of the invention in mammalian cells are the SV40 promoter (Subramani et al., *Mol. Cell Biol.* 1 (1981), 854–864), the MT-1 (metallothionein gene) promoter (Palmiter et al., *Science* 222 (1983), 809–814) or the adenovirus 2 major late promoter.

An example of a suitable promoter for use in insect cells is the polyhedrin promoter (U.S. Pat. No. 4,745,051; Vasuvedan et al., *FEBS Lett.* 311, (1992) 7–11), the P10 promoter (J. M. Vlak et al., *J. Gen. Virology* 69, 1988, pp. 765–776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., *J. Biol. Chem.* 255 (1980), 12073–12080; Alber and Kawasaki, J. Mol. Appl. Gen. 1 (1982), 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652–654) promoters.

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus subtilis* xylosidase gene, or by the phage Lambda $P_R$ or $P_L$ promoters or the *E. coli* lac, trp or tac promoters.

The DNA sequence encoding the polypeptide of the invention may also, if necessary, be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant vector of the invention may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid $2\mu$ replication genes REP 1–3 and origin of replication.

When the host cell is a bacterial cell, sequences enabling the vector to replicate are e.g. the Col E1 origin of replication as in pUC19 or pBR322 or the p15A origin of replication as in pACYC184 when the bacterium is *E. coli*. When the bacterium is B. subtilis the origin of replication from e.g. pUB10 is often used.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130), or one which confers resistance to a drug, e.g. ampicillin, kanamycin, tetracycline, chloramphenicol, neomycin, hygromycin or methotrexate. For filamentous fungi, selectable markers include amdS, pyrG, argB, niaD, sC.

To direct a polypeptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the polypeptide in the correct reading frame. Secretory signal sequences are commonly positioned 5' to the DNA sequence encoding the polypeptide. The secretory signal sequence may be that normally associated with the polypeptide or may be from a gene encoding another secreted protein.

For secretion from yeast cells, the secretory signal sequence may encode any signal peptide which ensures efficient direction of the expressed polypeptide into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., *Nature* 289, 1981, pp. 643–646), a modified carboxypeptidase signal peptide (cf. L. A. Valls et al., *Cell* 48, 1987, pp. 887–897), the yeast BAR1 signal peptide (cf. WO 87/02670), or the yeast aspartic protease 3 (YAP3) signal peptide (cf. M. Egel-Mitani et al., Yeast 6, 1990, pp. 127–137).

For efficient secretion in yeast, a sequence encoding a leader peptide may also be inserted downstream of the signal sequence and upstream of the DNA sequence encoding the polypeptide. The function of the leader peptide is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The leader peptide may be the yeast α-factor leader (the use of which is described in e.g. U.S. Pat. No. 4,546,082, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an Aspergillus sp. amylase or glucoamylase, a gene encoding a *Rhizomucor miehei* lipase or protease, or a gene encoding a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the present polypeptide, the promoter and optionally the terminator and/or secretory signal sequence, respectively, and to insert them into suitable vectors containing the information necessary for replication, are well known to persons skilled in the art (cf., for instance, Sambrook et al., op.cit.).

Host Cells

The DNA sequence encoding the present polypeptide introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a cDNA sequence encoding a polypeptide native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present polypeptide and includes bacteria, yeast, fungi and higher eukaryotic cells.

Examples of bacterial host cells which, on cultivation, are capable of producing the polypeptide of the invention are grampositive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis,* or strains of Streptomyces, such as *S. lividans* or *S. murinus,* or gramnegative bacteria such as *Echerichia coli.* The transformation of the bacteria may be effected by protoplast transformation or by using competent cells in a manner known per se (cf. Sambrook et al., supra).

When expressing the polypeptide in bacteria such as *E. coli,* the polypeptide may be retained in the cytoplasm, typically as insoluble granules (known as inclusion bodies), or may be directed to the periplasmic space by a bacterial secretion sequence. In the former case, the cells are lysed and the granules are recovered and denatured after which the polypeptide is refolded by diluting the denaturing agent. In the latter case, the polypeptide may be recovered from the periplasmic space by disrupting the cells, e.g. by sonication or osmotic shock, to release the contents of the periplasmic space and recovering the polypeptide.

Examples of suitable mammalian cell lines are the COS (ATCC CRL 1650), BHK (ATCC CRL 1632, ATCC CCL 10), CHL (ATCC CCL39) or CHO (ATCC CCL 61) cell lines. Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appl. Gene* 1 (1982), 327–341; Loyter et al., *Proc. Natl. Acad. Sci. USA* 79 (1982), 422–426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841–845.

Examples of suitable yeasts cells include cells of Saccharomyces spp. or Schizosaccharomyces spp., in particular strains of *Saccharomyces cerevisiae* or *Saccharomyces kluyveri.* Methods for transforming yeast cells with heterologous DNA and producing heterologous polypeptides therefrom are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the polypeptide of the invention may be preceded by a signal sequence and optionally a leader sequence , e.g. as described above. Further examples of suitable yeast cells are strains of Kluyveromyces, such as *K. lactis,* Hansenula, e.g. *H. polymorpha,* or Pichia, e.g. *P. pastoris* (cf. Gleeson et al., *J. Gen. Microbiol.* 132, 1986, pp. 3459–3465; U.S. Pat. No. 4,882,279).

Examples of other fungal cells are cells of filamentous fungi, e.g. Aspergillus spp., Neurospora spp., Fusarium spp. or Trichoderma spp., in particular strains of *A. oryzae, A. nidulans* or *A. niger.* The use of Aspergillus spp. for the expression of proteins is described in, e.g., EP 272 277 and EP 230 023. The transformation of *F. oxysporum* may, for instance, be carried out as described by Malardier et al., 1989, Gene 78: 147–156.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162,222; EP 397,485; all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting the expression of the present polypeptide, after which the resulting polypeptide is recovered from the culture.

The medium used for culturing the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The polypeptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

Transgenic Animals

It is also within the scope of the present invention to employ transgenic animal technology to produce the present polypeptide. A transgenic animal is one in whose genome a heterologous DNA sequence has been introduced. In particular, the polypeptide of the invention may be expressed in the mammary glands of a non-human female mammal, in particular one which is known to produce large quantities of milk. Examples of preferred mammals are livestock animals such as goats, sheep and cattle, although smaller mammals such as mice, rabbits or rats may also be employed.

The DNA sequence encoding the present polypeptide may be introduced into the animal by any one of the methods previously described for the purpose. For instance, to obtain expression in a mammary gland, a transcription promoter from a milk protein gene is used. Milk protein genes include the genes encoding casein (cf. U.S. Pat. No. 5,304,489), beta-lactoglobulin, alpha-lactalbumin and whey acidic protein. The currently preferred promoter is the beta-lactoglobulin promoter (cf. Whitelaw et al., Biochem J. 286, 1992, pp. 31–39). It is generally recognized in the art that DNA sequences lacking introns are poorly expressed in transgenic animals in comparison with those containing introns (cf. Brinster et al., Proc. Natl. Acad. Sci. U.S. Pat. No. 85, 1988, pp. 836–840; Palmiter et al., Proc. Natl. Acad. Sci. USA 88, 1991, pp. 478–482; Whitelaw et al., Transgenic Res. 1, 1991, pp. 3–13; WO 89/01343; WO 91/02318). For expression in transgenic animals, it is therefore preferred, whenever possible, to use genomic sequences containing all or some of the native introns of the gene encoding the polypeptide of interest. It may also be preferred to include at least some introns from, e.g. the beta-lactoglobulin gene. One such region is a DNA segment which provides for intron splicing and RNA polyadenylation from the 3' non-coding region of the ovine beta-lactogloblin gene. When substituted for the native 3' non-coding sequences of a gene, this segment will enhance and stabilise expression levels of the polypeptide of interest. It may also be possible to replace the region surrounding the initiation codon of the polypeptide of interest with corresponding sequences of a milk protein gene. Such replacement provides a putative tissue-specific initiation environment to enhance expression.

For expression of the present polypeptide in transgenic animals, a nucleotide sequence encoding the polypeptide is operably linked to additional DNA sequences required for its expression to produce expression units. Such additional sequences include a promoter as indicated above, as well as sequences providing for termination of transcription and polyadenylation of mRNA. The expression unit further includes a DNA sequence encoding a secretory signal sequence operably linked to the sequence encoding the polypeptide. The secretory signal sequence may be one native to the polypeptide or may be that of another protein such as a milk protein (cf. von Heijne et al., Nucl. Acids Res. 14, 1986, pp. 4683-4690; and U.S. Pat. No. 4,873,316).

Construction of the expression unit for use in transgenic animals may conveniently be done by inserting a DNA sequence encoding the present polypeptide into a vector containing the additional DNA sequences, although the expression unit may be constructed by essentially any sequence of ligations. It is particularly convenient to provide a vector containing a DNA sequence encoding a milk protein and to replace the coding region for the milk protein with a DNA sequence coding for the present polypeptide, thereby creating a fusion which includes expression control sequences of the milk protein gene.

The expression unit is then introduced into fertilized ova or early-stage embryos of the selected host species. Introduction of heterologous DNA may be carried out in a number of ways, including microinjection (cf. U.S. Pat. No. 4,873,191), retroviral infection (cf. Jaenisch, *Science* 240, 1988, pp. 1468–1474) or site-directed integration using embryonic stem cells (reviewed by Bradley et al., *Bio/Technology* 10, 1992, pp. 534–539). The ova are then implanted into the oviducts or uteri of pseudopregnant females and allowed to develop to term. Offspring carrying the introduced DNA in their germ line can pass the DNA on to their progeny, allowing the development of transgenic herds.

General procedures for producing transgenic animals are known in the art, cf. for instance, Hogan et al., *Manipulating the Mouse Embryo: A Laboratory Manual,* Cold Spring Harbor Laboratory, 1986; Simons et al., *Bio/Technology* 6, 1988, pp. 179–183; Wall et al., *Biol. Reprod.* 32, 1985, pp. 645–651; Buhler et al., *Bio/Technology* 8, 1990, pp. 140–143; Ebert et al., *Bio/Technology* 6: 179–183, 1988; Krimpenfort et al., *Bio/Technology* 9: 844–847, 1991, Wall et al., *J. Cell. Biochem.* 49: 113–120, 1992; U.S. Pat. No. 4,873,191, U.S. Pat. No. 4,873,316; WO 88/00239, WO 90/05188; WO 92/11757 and GB 87/00458. Techniques for introducing heterologous DNA sequences into mammals and their germ cells were originally developed in the mouse. See, e.g. Gordon et al., *Proc. Natl. Acad. Sci. USA* 77: 7380–7384, 1980, Gordon and Ruddle, *Science* 214: 1244–1246, 1981; Palmiter and Brinster, *Cell* 41: 343-345, 1985; Brinster et al., *Proc. Natl. Acad. Sci. USA* 82:

4438–4442, 1985; and Hogan et al. (ibid.). These techniques were subsequently adapted for use with larger animals, including livestock species (see e.g., WO 88/00239, WO 90/01588 and WO 92/11757; and Simons et al., Bio/Technoloy 6: 179–183, 1988). To summarize, in the most efficient route used to date in the generation of transgenic mice or livestock, several hundred linear molecules of the DNA of interest are injected into one of the pro-nuclei of a fertilized egg according to techniques which have become standard in the art. Injection of DNA into the cytoplasm of a zygote can also be employed.

Transgenic Plants

Production in transgenic plants may also be employed.

It has previously been described to introduce DNA sequences into plants, which sequences code for protein products imparting to the transformed plants certain desirable properties such as increased resistance against pests, pathogens, herbicides or stress conditions (cf. for instance EP 90 033, EP 131 620, EP 205 518, EP 270 355, WO 89/04371 or WO 90/02804), or an improved nutrient value of the plant proteins (cf. for instance EP 90 033, EP 205 518 or WO 89/04371). Furthermore, WO 89/12386 discloses the transformation of plant cells with a gene coding for levansucrase or dextransucrase, regeneration of the plant (especially a tomato plant) from the cell resulting in fruit products with altered viscosity characteristics.

In the plant cell, the DNA sequence encoding the present polypeptide is under the control of a regulatory sequence which directs the expression of the polypeptide from the DNA sequence in plant cells and intact plants. The regulatory sequence may be either endogenous or heterologous to the host plant cell.

The regulatory sequence may comprise a promoter capable of directing the transcription of the DNA sequence encoding the polypeptide in plants. Examples of promoters which may be used according to the invention are the 35s RNA promoter from cauliflower mosaic virus (CaMV), the class I patatin gene B 33 promoter, the ST-LS1 gene promoter, promoters conferring seed-specific expression, e.g. the phaseolin promoter, or promoters which are activated on wounding, such as the promoter of the proteinase inhibitor II gene or the wun1 or wun2 genes.

The promoter may be operably connected to an enhancer sequence, the purpose of which is to ensure increased transcription of the DNA sequence encoding the polypeptide. Examples of useful enhancer sequences are enhancers from the 5'-upstream region of the 35s RNA of CaMV, the 5'-upstream region of the ST-LS1 gene, the 5'-upstream region of the Cab gene from wheat, the 5'-upstream region of the 1'- and 2'-genes of the $T_R$-DNA of the Ti plasmid pTi ACH5, the 5'-upstream region of the octopine synthase gene, the 5'-upstream region of the leghemoglobin gene, etc.

The regulatory sequence may also comprise a terminator capable of terminating the transcription of the DNA sequence encoding the polypeptide in plants. Examples of suitable terminators are the terminator of the octopine synthase gene of the T-DNA of the Ti-plasmid pTiACH5 of Agrobacterium tumefaciens, of the gene 7 of the T-DNA of the Ti plasmid pTiACH5, of the nopaline synthase gene, of the 35s RNA-coding gene from CaMV or from various plant genes, e.g. the ST-LS1 gene, the Cab gene from wheat, class I and class II patatin genes, etc.

The DNA sequence encoding the polypeptide may also be operably connected to a DNA sequence encoding a leader peptide capable of directing the transport of the expressed polypeptide to a specific cellular compartment (e.g. vacuoles) or to extracellular space. Examples of suitable leader peptides are the leader peptide of proteinase inhibitor II from potato, the leader peptide and an additional about 100 amino acid fragments of patatin, or the transit peptide of various nucleus-encoded proteins directed into chloroplasts (e.g. from the St-LS1 gene, SS-Rubisco genes, etc.) or into mitochondria (e.g. from the ADP/ATP translocator).

Furthermore, the DNA sequence encoding the polypeptide may be modified in the 5' non-translated region resulting in enhanced translation of the sequence. Such modifications may, for instance, result in removal of hairpin loops in RNA of the 5' non-translated region. Translation enhancement may be provided by suitably modifying the omega sequence of tobacco mosaic virus or the leaders of other plant viruses (e.g. BMV, MSV) or of plant genes expressed at high levels (e.g. SS-Rubisco, class I patatin or proteinase inhibitor II genes from potato).

The DNA sequence encoding the polypeptide may furthermore be connected to a second DNA sequence encoding another polypeptide or a fragment thereof in such a way that expression of said DNA sequences results in the production of a fusion protein. When the host cell is a potato plant cell, the second DNA sequence may, for instance, encode patatin or a fragment thereof (such as a fragment of about 100 amino acids).

The plant in which the DNA sequence coding for the polypeptide is introduced may suitably be a dicotyledonous plant, examples of which are is a tobacco, potato, tomato, or leguminous (e.g. bean, pea, soy, alfalfa) plant. It is, however, contemplated that mono-cotyledonous plants, e.g. cereals, may equally well be transformed with the DNA sequence coding for the enzyme.

Procedures for the genetic manipulation of monocotyledonous and dicotyledonous plants are well known. In order to construct foreign genes for their subsequent introduction into higher plants, numerous cloning vectors are available which generally contain a replication system for E. coli and a selectable/screenable marker system permitting the recognition of transformed cells. These vectors include e.g. pBR322, the pUC series, pACYC, M13 mp series etc. The foreign sequence may be cloned into appropriate restriction sites. The recombinant plasmid obtained in this way may subsequently be used for the transformation of E. coli. Transformed E. coli cells may be grown in an appropriate medium, harvested and lysed. The chimeric plasmid may then be reisolated and analyzed. Analysis of the recombinant plasmid may be performed by e.g. determination of the nucleotide sequence, restriction analysis, electrophoresis and other molecular-biochemical methods. After each manipulation the sequence may be cleaved and ligated to another DNA sequence. Each Is DNA sequence can be cloned on a separate plasmid DNA. Depending on the way used for transferring the foreign DNA into plant cells other DNA sequences might be of importance. In case the Ti-plasmid or the Ri plasmid of Agrobacterium tumefaciens or Agrobacterium rhizogenes, at least the right border of the T-DNA may be used, and often both the right and the left borders of the T-DNA of the Ri or Ti plasmid will be present flanking the DNA sequence to be transferred into plant cells.

The use of the T-DNA for transferring foreign DNA into plant cells has been described extensively in the prior literature (cf. Gasser and Fraley, 1989, Science 244, 1293–1299 and references cited therein). After integration of the foreign DNA into the plant genome, this sequence is fairly stable at the original locus and is usually not lost in subsequent mitotic or meiotic divisions. As a general rule, a selectable marker gene will be cotransferred in addition to the gene to be transferred, which marker renders the plant cell resistant to certain antibiotics, e.g. kanamycin, hygromycin, G418 etc. This marker permits the recognition of the transformed cells containing the DNA sequence to be transferred compared to nontransformed cells.

Numerous techniques are available for the introduction of DNA into a plant cell. Examples are the Agrobacterium mediated transfer, the fusion of protoplasts with liposomes containing the respective DNA, microinjection of foreign DNA, electroporation etc. In case Agrobacterium mediated gene transfer is employed, the DNA to be transferred has to be present in special plasmids which are either of the intermediate type or the binary type. Due to the presence of sequences homologous to T-DNA sequences, intermediate vectors may integrate into the Ri- or Ti-plasmid by homologous recombination. The Ri- or Ti-plasmid additionally contains the vir-region which is necessary for the transfer of the foreign gene into plant cells. Intermediate vectors cannot replicate in Agrobacterium species and are transferred into Agrobacterium by either direct transformation or mobilization by means of helper plasmids (conjugation). (Cf. Gasser and Fraley, op. cit. and references cited therein).

Binary vectors may replicate in both Agrobacterium species and *E. coli*. They may contain a selectable marker and a poly-linker region which to the left and right contains the border sequences of the T-DNA of *Agrobacterium rhizogenes* or *Agrobacterium tumefaciens*. Such vectors may be transformed directly into Agrobacterium species. The Agrobacterium cell serving as the host cell has to contain a vir-region on another plasmid. Additional T-DNA sequences may also be contained in the Agrobacterium cell.

The Agrobacterium cell containing the DNA sequences to be transferred into plant cells either on a binary vector or in the form of a cointegrate between the intermediate vector and the T-DNA region may then be used for transforming plant cells. Usually either multicellular explants (e.g. leaf discs, stem segments, roots), single cells (protoplasts) or cell suspensions are cocultivated with Agrobacterium cells containing the DNA sequence to be transferred into plant cells. The plant cells treated with the Agrobacterium cells are then selected for the cotransferred resistance marker (e.g. kanamycin) and subsequently regenerated to intact plants. These regenerated plants will then be tested for the presence of the DNA sequences to be transferred.

If the DNA is transferred by e.g. electroporation or microinjection, no special requirements are needed to effect transformation. Simple plasmids e.g. of the pUC series may be used to transform plant cells. Regenerated transgenic plants may be grown normally in a greenhouse or under other conditions. They should display a new phenotype (e.g. production of new proteins) due to the transfer of the foreign gene(s). The transgenic plants may be crossed with other plants which may either be wild-type or transgenic plants transformed with the same or another DNA sequence. Seeds obtained from transgenic plants should be tested to assure that the new genetic trait is inherited in a stable Mendelian fashion.

See also Hiatt, Nature 344: 469–479, 1990; Edelbaum et al., J. Interferon Res. 12: 449–453, 1992; Sijmons et al., Bio/Tecnology 8: 217–221, 1990: and EP 255 378.

Uses

In the pharmaceutical composition of the invention, the present polypeptide may be formulated by any of the established methods of formulating pharmaceutical compositions, e.g. as described in *Remington's Pharmaceutical Science*, 19 th. edition, 1995. The composition may be in a form suited for systemic injection or infusion and may, as such, be formulated with sterile water or an isotonic saline or glucose solution. The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

The pharmaceutical composition of the present invention may also be adapted for oral, nasal, transdermal, transepithelial or rectal administration. The pharmaceutically acceptable carrier or diluent employed in the composition may be any conventional solid carrier. Examples of solid carriers are lactose, terra alba, sucrose, talc, gelatin, agar, pectin, acacia, magnesium stearate and stearic acid. Similarly, the carrier or diluent may include any sustained release material known in the art, such as glyceryl monostearate or glyceryl distearate, alone or mixed with a wax. For oral administration, the composition may be tabletted, placed in a hard gelatin capsule in powder or pellet form or it can be in the form of a troche or lozenge. The amount of solid carrier will vary widely but will usually be from about 25 mg to about 1 g. The present polypeptide may also be placed in a soft gelatin capsule in a liquid carrier such as syrup, peanut oil, olive oil or water.

The polypeptides of the invention are effective over a wide dosage range. A typical dosage is in the range of from 0.05 to about 1000 mg, preferably from about 0.1 to about 500 mg, and more preferred from about 0.5 mg to about 200 mg per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated as well as other factors evident to those skilled in the art.

The polypeptide of the invention is contemplated to be advantageous for use in therapeutic applications within appetite suppression or satiety induction, such as for the prophylaxis or treatment of diseases or disorders associated with impaired appetite regulation. Examples of such diseases or disorders are obesity, type II diabetes and bulimia. The dosage of the polypeptide administered to a patient will vary with the type and severity of the condition to be treated, but is generally in the range of 0.01–5.0 mg/kg body weight per day in one or more dosages such as 1 to 3 dosages.

Furthermore, the polypeptide of the invention is contemplated to be advantageous for treatment of autoimmune disorders, inflammation, arthritis, type I diabetes, multiple schlerosis, stroke, osteoporosis, septic shock, symptoms of menopause, menstrual complications and Parkinson's disease.

The present invention is further illustrated by the following representative examples which are, however, not intended to limit the scope of the invention in any way. Fur further details of the invention reference should also be made to Peter Kristensen et al., "Hypothalamic CART: a novel anorectic peptide regulated by leptin", Nature, in press, which is hereby incorporated by reference.

EXAMPLES

Example 1

Isolation of CART

Total RNA from cultivated cells were prepared from primary cell lines derived from the rat tumors MSL-A-AN and MSL-A-M3 (Madsen et al, *Scand. J. Clin. Invest.* Supplement 220: 27–36) by the method of Chomczynski & Sacchi (1987). From this we made poly-A mRNA using Pharmacia's "Quick Prep® micro" mRNA purification kit. Double stranded cDNA was made using Clontech's "cDNA clone I" synthesis kit. Eco RI adaptors CA6/CA7 (Ace et al. (1994)) were added to the blunt ended cDNA's. 50 ng of each cDNA was amplified using the CA6 primer. The primer used for amplification of the MSL-A-M3 cDNA was biotinylated (the driver). The amplified MSL-A-AN cDNA was cut with Eco RI (the tracer). 8 μg of the biotinylated M3 cDNA was bound to 60 μl of DYNAL magnetic streptavidin beads, treated with NaOH, washed, 2× hybridization buffer was added, and the mixture was heated to 68° C. 0.5 μg of the Eco RI cut AN cDNA was heated to 98° C. and added to the tube with the magnetic beads. The reaction tube was incubated at 68° C. for 20 hours. The magnetic beads with the bound cDNA and the tracer which had hybridized to it was removed using a magnet.

This procedure was repeated three times, the last two with 10 μg of driver DNA and 80 μl of magnetic beads.

The remaining tracer DNA was purified on a Chromaspin 100 column from Clontech and cloned into an Eco RI cut vector (pCRTmI, Invitrogen) and transformed into *E. coli* (ElectroMax).

The cells were plated on LB plates with 100 μg/ml Ampicillin. The plates were replicated and the cells from the replica were transferred to nylon filters (Hybond-N +, Amersham). The filters were hybridized with radioactively labelled driver cDNA and autoradiographs were made. The filters were then stripped for the radioactive probe and thereafter the procedure was repeated with a probe made from the tracer cDNA.

The autoradiographs were compared and spots that were only present with the latter probe were identified and the corresponding colonies were isolated.

DNA sequencing of the inserted DNA in one of these colonies were identified as CART (Cocaine and Amphetamine Regulated Transcript from rat brain (Douglass et al. (1995)). This transcript codes for a protein (polypeptide) of 129 or 116 amino acids (differential splicing of an in frame 39 bp intron). The polypeptide seems to have a signal sequence in the amino terminal end, and the secreted part contains several dibasic amino acid pairs which could be "pro hormone" processing sites.

Example 2

Cloning of Rat CART

In order to clone the whole coding region of the CART gene primers were made that overlaps with the start codon and with the stop codon, respectivly.
MHJ4754:  5'-AAAAAGGATCCACC ATGGAGAGCTCCCGCC-3'
Bold: Bam HI site for cloning. Underlined: ATG start codon.
MHJ4753:  5'-AAAAAAGCT TCACAAGCACTTCAAGAGGAAA-3'
Bold: Hin dIII site for cloning. Underlined: TGA stop codon, opposite strand.

As template for the PCR cloning we used the same double stranded cDNA preparation as described in Example 1 (from MSL-A-AN).

The PCR reaction, 25 cycles:
60 sec 94° C.
30 sec 52° C.
60 sec 72° C.

Two bands appeared when the reaction mix was run on a 2% agarose gel corresponding to the two splice variants mentioned in Douglass et al. (1995).

Each of the two bands were isolated, cut with Bam HI and Hin dIII, and cloned into Bam HI-Hin dIII cut pSX221 (fragments A,B,C,D, and E ligated into pSX191, WO 92/11357) giving rise to pSX592 and pSX593 (short and long form, respectively) corresponding to SEQ ID Nos. 2 and 1, respectively (see FIG. 1).

Example 3

Expression of Rat CART in *E. coli* I

In order to express CART in *E. coli* three constructs were made where different forms of CART were fused to Glutathione S-transferase using the pGEX system from Pharmacia P-L Biochemicals.

The different forms of CART, full length of both splice variants (starting with Gln-Glu-Asp) and the form starting with Ile-Pro-Ile (Spiess et al. (1981)) were amplified using PCR primers that add a Bam HI site (bold) and the four triplets that codes for the Factor Xa protease recognition site Ile-Glu-Gly-Arg in the 5'-end (N-terminus). As 3'-end primer we used the same as in Example 2 (MHJ4753). As templates were used the plasmids pSX592 and pSX593 described in Example 2.

MHJ4885: 5'-AAA AGGATCC ATC GAA GGT CGT CAG GAG GAT GCC GAG CTG-3' Ile Glu Gly Arg Gln Glu Asp Ala Ser Leu

MHJ4880: 5'-AAAAAGGATCC ATC GAA GGT CGT ATT CCG ATC TAT GAG AAG A-3' Ile Glu Gly Arg Ile Pro Ile Tyr Glu Lys

The PCR reaction, 25 cycles:
60 sec 94° C.
30 sec 55° C.
60 sec 72° C.

Figure 2:
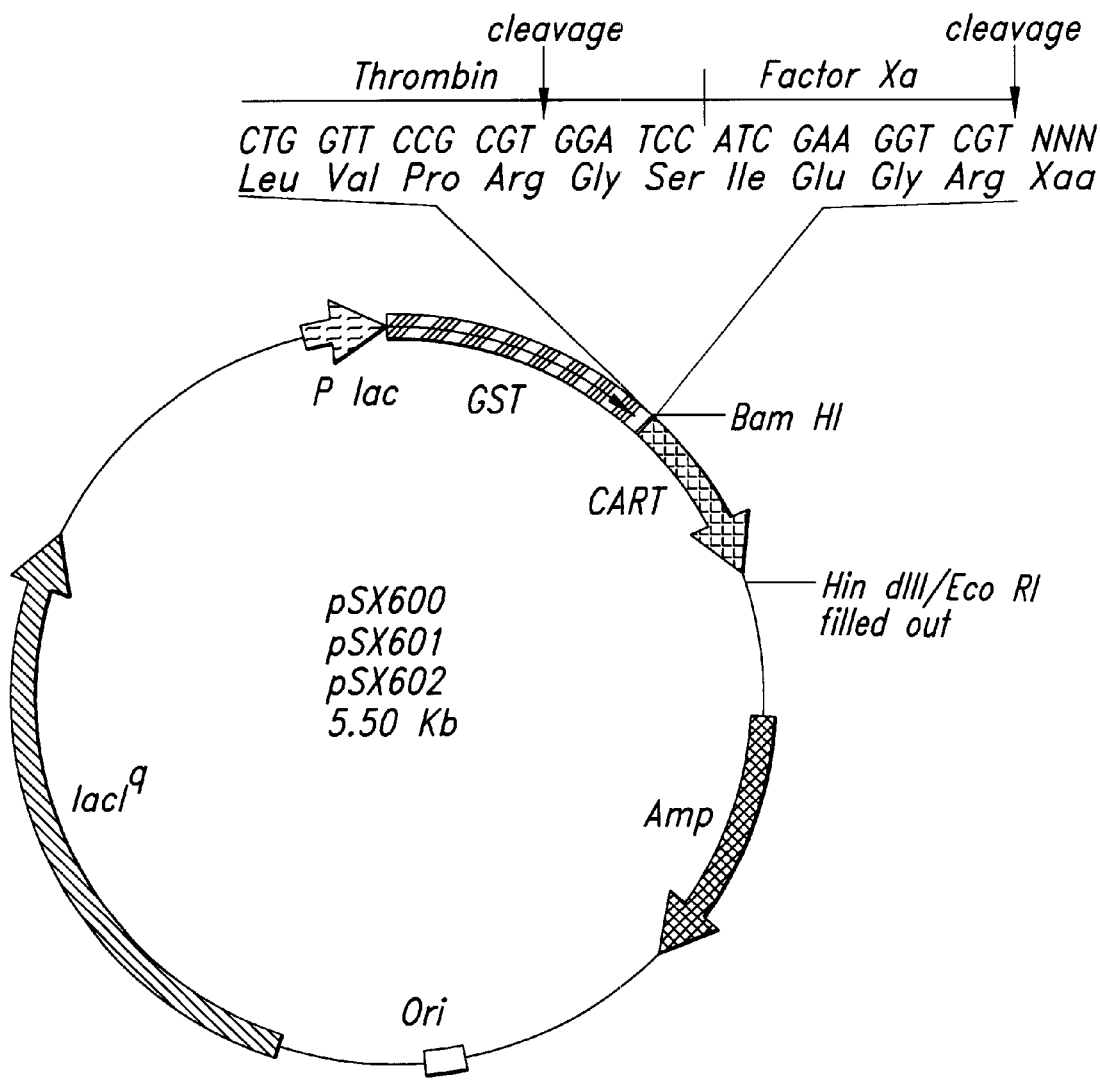
FIG. 2. Expression in *E. coli*. Fusion to Glutathione-S-transferase.

The reaction mixtures were cut with Hin dIII, filled out with Klenow polymerase, and then cut with Bam HI. They were then run on a 2% agarose gel and the bands corresponding to the three variants were isolated and cloned into pGEX-2T (cut with Eco RI, filled out, and then cut with Bam HI) giving rise to pSX600 (IPI-CART) corresponding to SEQ ID No. 4, pSX 601 (short form) corresponding to SEQ ID No. 2, and pSX605 (long form) corresponding to SEQ ID No. 1 (see FIG. 2).

Example 4

Expression of rat CART in *E. coli* II

In order to express CART in *E. coli* three constructs were made where different forms of CART were fused to Thioredoxin using the ThioFusion™ Expression System from Invitrogen Corporation.

The different forms of CART, full length of both splice variants (starting with Gln-Glu-Asp) and the form starting with Ile-Pro-Ile (Spiess et al. (1981)) were amplified using PCR primers that add a Bam HI site (bold) and the four triplets that codes for the Factor Xa protease recognition site Ile-Glu-Gly-Arg in the 5'-end (N-terminus) and a Hin dIII (bold) site in the 3'-end. As templates were used the pGEX fusion constructs described in Example 3.

MHJ5141: 5'-AAAAAGGATCCG ATC GAA GGT CGT CAG GAG GAT-3' Ile Glu Gly Arg Gln Glu Asp

MHJ5140: 5'-AAAAAGGATCCG ATC GAA GGT CGT ATT CCG ATC-3' Ile Glu Gly Arg Ile Pro Ile

M H J 5 1 4 2 :
5-AAAAAGTCGATAAGCTTCACAAGCACTTC AAGAGGA-3'

Bold: Hin dIII Underlined: Stop codon on opposite strand

The PCR reaction, 25 cycles:

60 sec 94° C.

30 sec 52° C.

60 sec 72° C.

Figure 3:
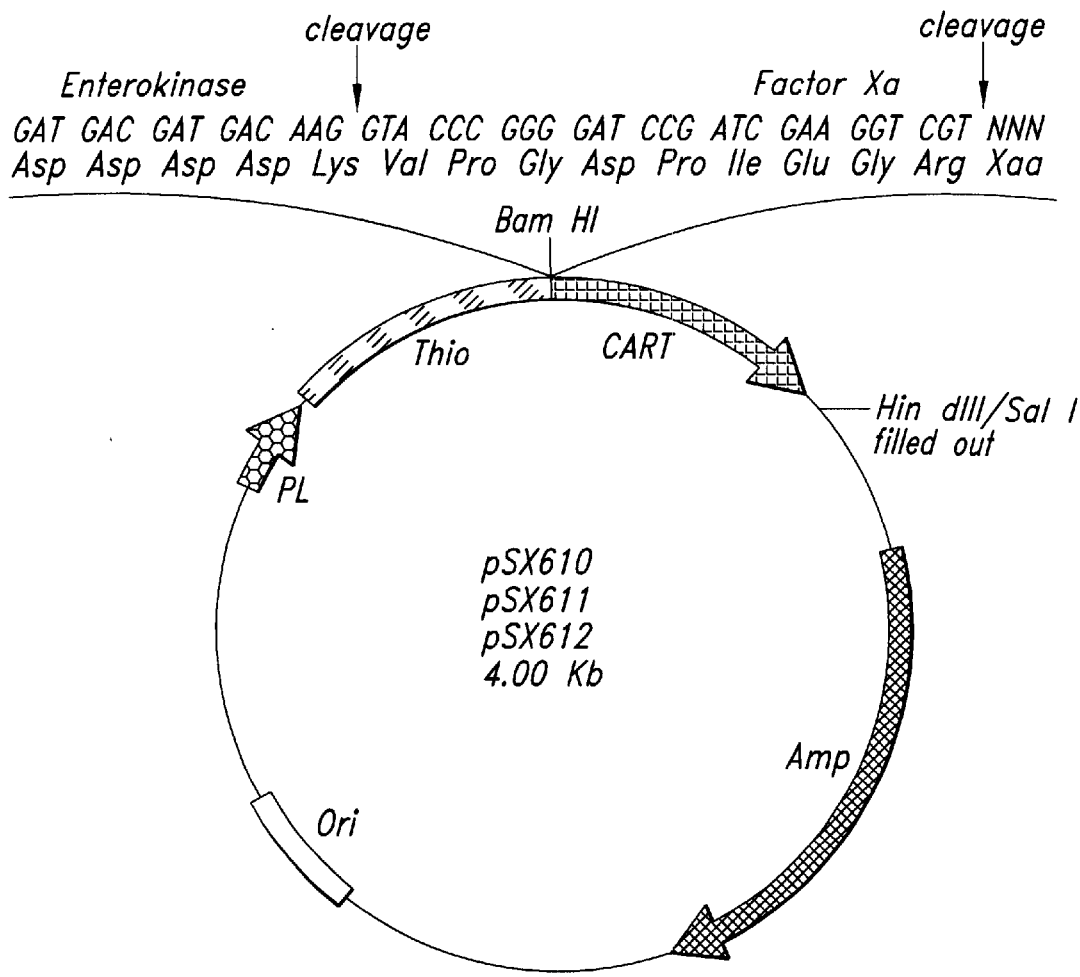
FIG. 3: Expression in *E. coli*. Fusion to Thioredoxin.

The reaction mixtures were cut with Hin dIII, filled out with Klenow polymerase and then cut with Bam HI. They were then run on a 2% agarose gel and the bands corresponding to the three variants were isolated and cloned into pTrxFus (cut with Sal I, filled out, and then cut with Bam HI) giving rise to pSX610 (long form) corresponding to SEQ ID No. 1, pSX611 (short form) corresponding to SEQ ID No. 2, and pSX612 (IPI-CART) corresponding to SEQ ID No. 4 (see FIG. 3).

The plasmids were transformed into *E. Coli* G1724 (Invitrogen) and the the resulting strains were cultivated according to the manual for the ThioFusion™ Expression System kit.

The fusion proteins were purified according to the instruction manual for ThioBond™ Resin (Invitrogen Corporation). The purified fusion proteins were then treated with the endoproteinase Factor Xa (Boehringer Mannheim). Ratio Factor Xa/Fusion protein=1/800. Incubation: 4° C., 16 hours.

Example 5

Expression of Rat CART in *S. cerevisiae*

The Yeast-*E.coli* shuttle vector used in the following example (pAK405) contains a heterologous protein expression cassette, which includes a DNA sequence encoding a modified MFα1 leader sequence (with a NcoI site added in the 3'-end) followed by the heterologous polypeptide in question operably placed in between the TPI promoter and the TPI terminator of *S. cerevisiae* in a POT plasmid (Kjeldsen et al., Gene 170:107–112, 1996).

Two primers CART1 and CART2 were constructed. These allow a PCR product to be made that furnishes the DNA sequence encoding either the short or the long form of full length CART with a 5' NcoI site and a 3' XbaI site allowing insertion into the yeast-*E.coli* shuttle vector pAK405.

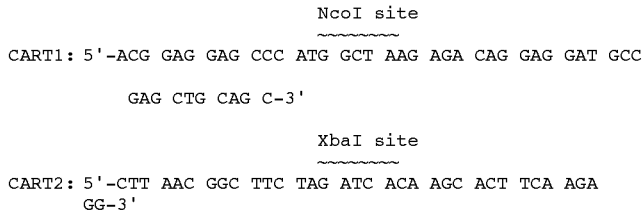

CART1: 5'-ACG GAG GAG CCC ATG GCT AAG AGA CAG GAG GAT GCC GAG CTG CAG C-3'

CART2: 5'-CTT AAC GGC TTC TAG ATC ACA AGC ACT TCA AGA GG-3'

The following Polymerase Chain Reaction (PCR) was performed using the Pwo DNA polymerase (Boehringer Mannheim) according to the manufacturers instructions.

5 µl primer CARTI (100 pmol)

5 µl primer CART2 (100 pmol)

10 µl 10×PCR buffer+MgSO$_4$

8 µl dNTP mix 0.5 µl Pwo enzyme

1 µl pSX592 or pSX593 plasmid as template (0.2 µg DNA)

25 70.5 1 H$_2$O

A total of 16 cycles was performed. One cycle was as follows: 45 sec at 94° C., 1 min at 42° C, and 1.5 min at 72° C.

Figure 4:
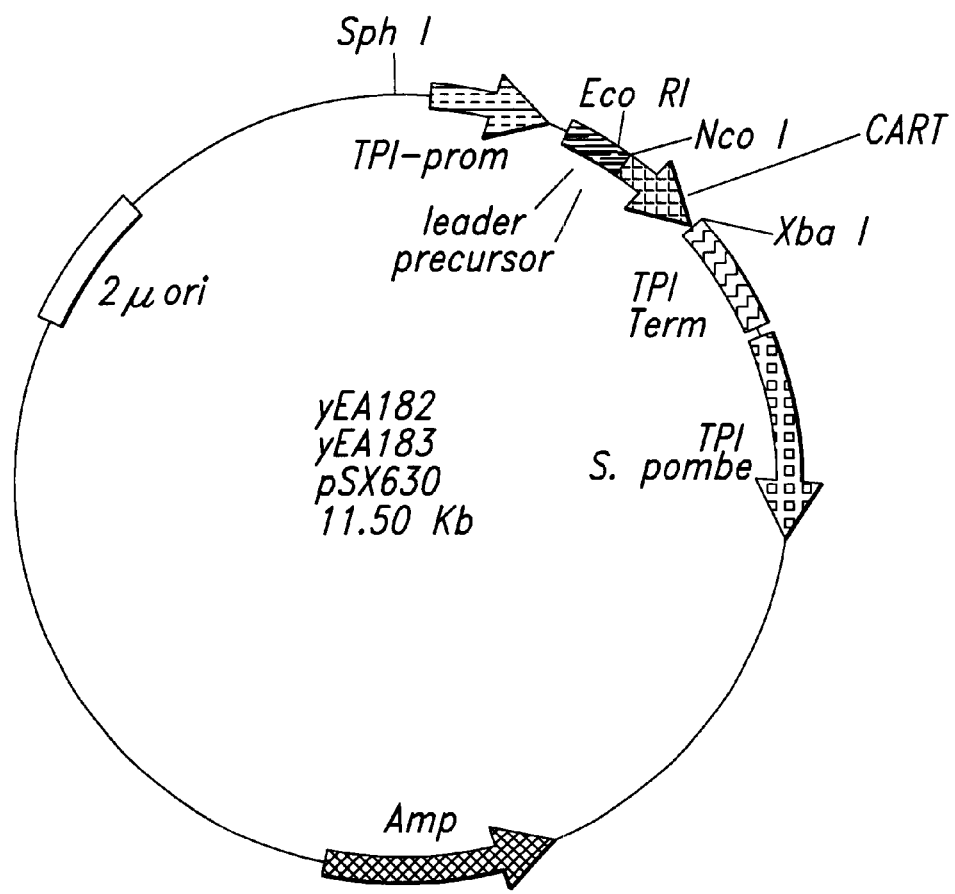
FIG. 4: Expression of CART in yeast.

The resulting PCR products were cut with restriction enzymes NcoI and XbaI and ligated with the BstXI/XbaI fragment and the BstXI/NcoI fragment of pAK405. BstXI, NcoI and XbaI cutat positions 701, 1419 and 1616 of pAK405, respectively. The construction and DNA sequence of the resulting heterologous expression cassettes are shown in FIGS. 4 and 5, respectively.

The resulting plasmids pEA182 (short form of CART) and pEA183 (long form of CART) were transformed into *S. cerevisia* strain ME1487 (MATαΔyap3::URA3 pep4–3 Δtpi::LEU2 leu2 HIS4 ΔURA3, described in patent application DK 0749/96).

Transformants were selected by glucose utilization as a carbon source in YPD plates (1% w/v yeast extract, 2% w/v peptone, 2% glucose, 2% agar). yEA182 corresponding to SEQ ID No. 2 and yEA183 corresponding to SEQ ID No. 1 are the transformants obtained from the plasmids pEA182 and pEA183, respectively.

A similar construct was made which produces IPI-CART: pSX630 corresponding to SEQ ID No. 4.

Transformants were cultivated in YPD liquid medium at 30° C. for 3 days with shaking at 200 rpm. Culture supernatants were obtained after centrifugation and supernatants were analysed for CART related material.

Human CART(1–89) corresponding to SEQ ID No. 3 differs from the rat form by having a valine residue in position 42 in stead of a isoleucine residue. Human CART (1–89) may be prepared in analogy with the above examples starting from a human tissue or simply by substituting valine for isoleucine in position 42 of rat CART(1–89) according to methods well-known to a person skilled in the art.

Example 6

Preparation of Rat CART(68–102, Long), SEQ ID No. 9

Ten mg of rat CART(54–102, long), SEQ ID No.6, prepared as described in Example 7, was dissolved in 2 ml of 70% (v/v) formic acid. A crystal corresponding to approx. 1 mg of cyanogenebromide was added to the dissolved peptide and the mixture was allowed to stand dark at room temperature for 16 hours. The generated CART fragment, CART(68-102, long) was purified by preparative HPLC as described in Example 7.

Example 7

E.Coli Construction

The thioredoxin-CART short form fusion protein was isolated from 2 liters of E.Coli fermentation broth and subjected to FXa cleavage.

Figure 6:
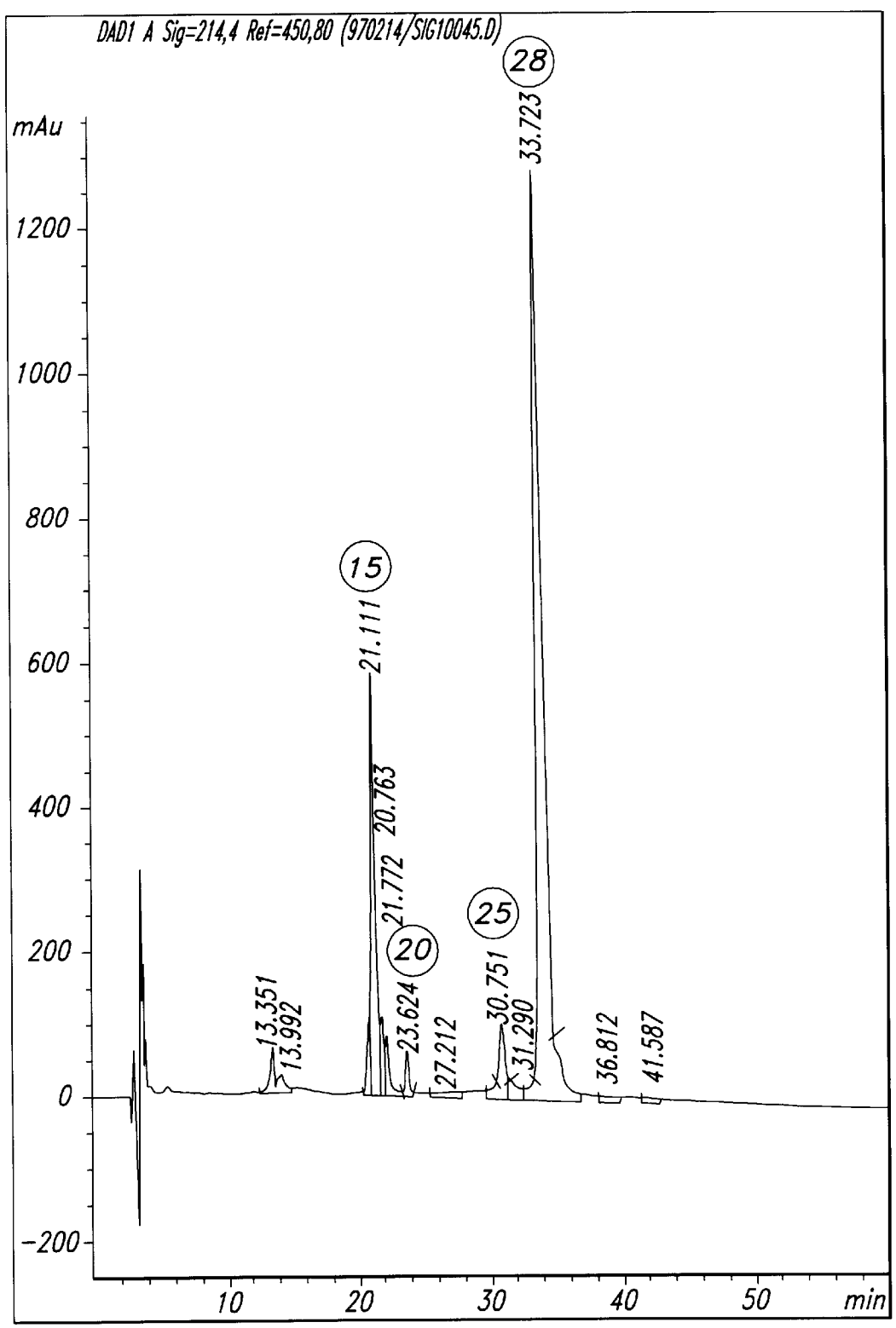
FIG. 6: Preparation of FXa-digest of the thioredoxin-CART fusion protein.

This digest mixture was analysed by HPLC (FIG. 6). Fractions corresponding to the two main peaks (Fr. 15 and Fr. 28, FIG. 6) were subjected to sequence and mass spectrometry analysis:

| Fr. No. | Sequence found | Mass found | Theoretical mass |
| --- | --- | --- | --- |
| 15 | ALDIYSAVDD... | 8882.8 | 8882.4 |
| 28 | SDKIIHLTDD... | 13529.0 | 13529.5 |

The peptide found in Fraction 15 is identical to rat CART(10–89) corresponding to SEQ ID No. 10, whereas the peptide in Fraction 28 is the thioredoxin split product with the C-terminal sequence of... IEGR. The small peptide fragment, CART(1–9), was not identified in the digest.

From 2 l of fermentation broth the total of 4.0 mg of CART(10–89) was isolated.

Human CART(10–89) corresponding to SEQ ID No. 11 differs from the rat form by having a valine residue in position 33 in stead of a isoleucine residue. Human CART (10–89) may be prepared in analogy with the above example starting from a human tissue or simply by substituting valine for isoleucine in position 33 of rat CART(10–89) according to methods well-known to a person skilled in the art.

Yeast Construction

Figure 7:
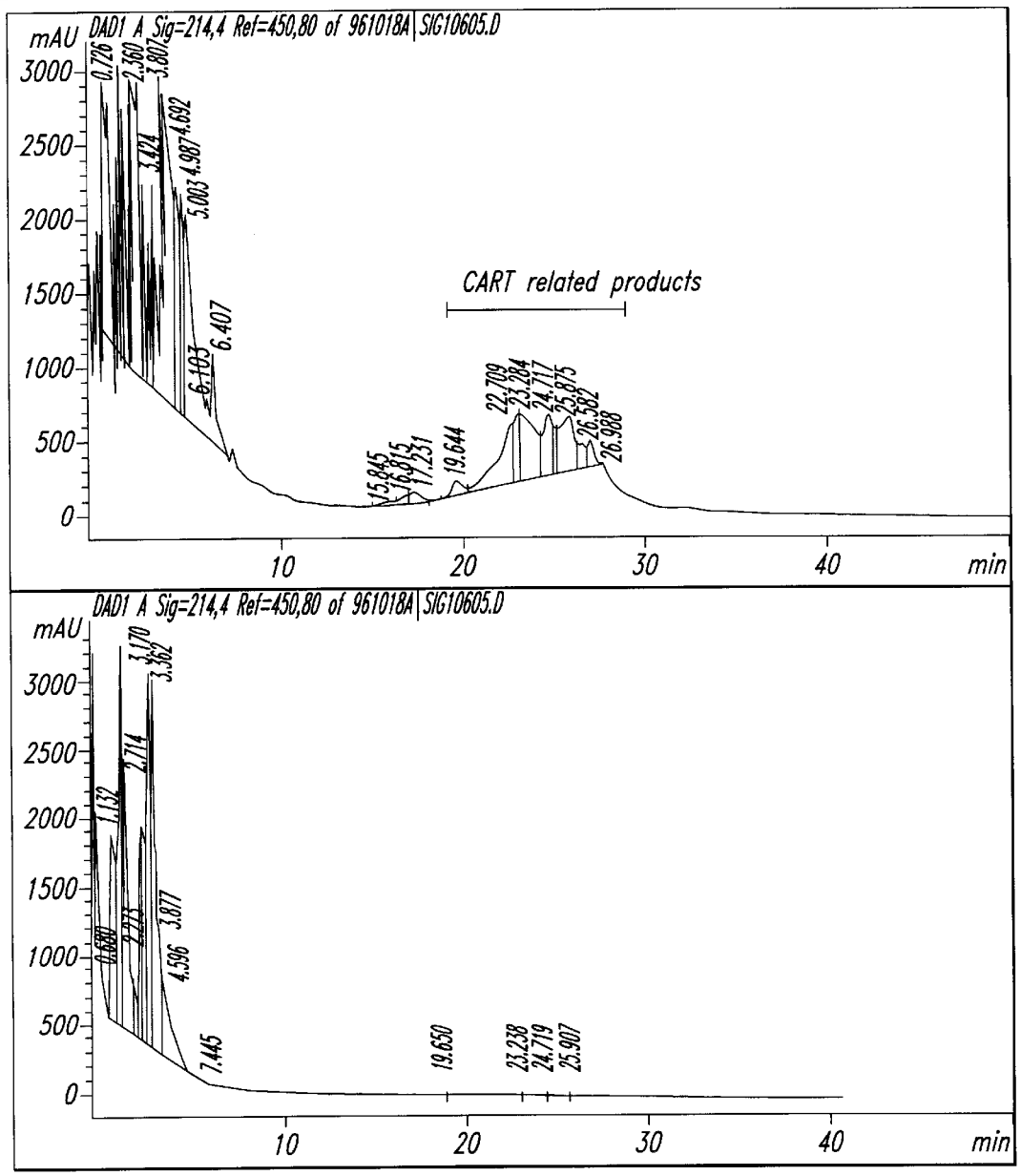
FIG. 7: Analytical HPLC of CART yeast supernatant H-372.

The fermentation broth from the 5 liters yeast fermentation (yEA183, long form) was analysed by HPLC (FIG. 7). A series of expression products was seen in this analysis.

Preliminary sequence analysis indicated that several of the peptides eluting at a retention time between 20 and 30 min. were fragments of the mature full length CART molecule.

The total amount of CART related products in the fermentation broth was approx. 250 mg/liter.

Figure 8:
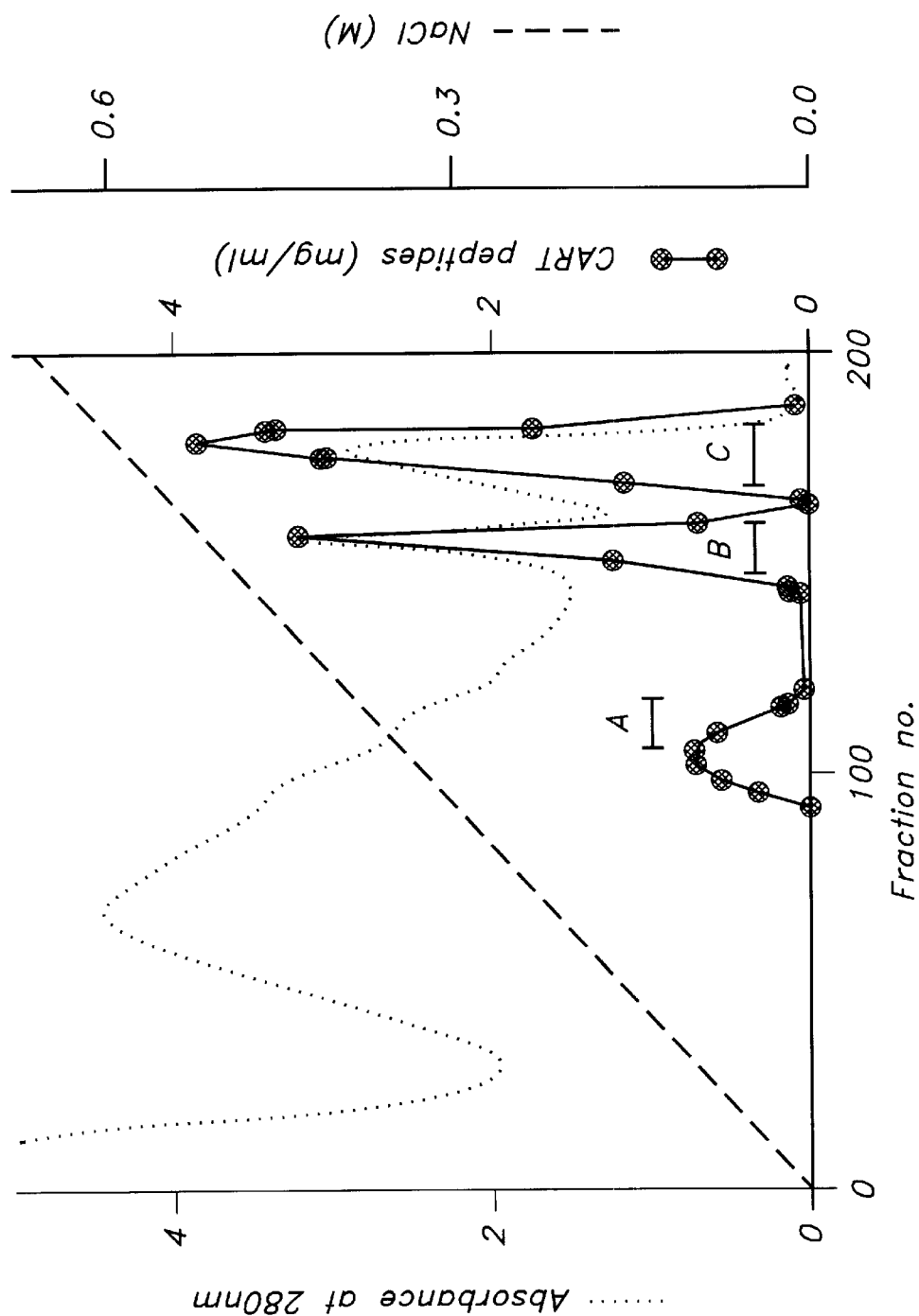
FIG. 8: SP-Sepharose Column.

The CART fragments from 4.25 liters of fermentation broth were separated using the following method:

The fermentation broth (pH=4.6, Λ=8 mS) was adjusted to pH=5.0 and diluted with 25 liters of water (resulting Λ=1.3 mS) and pumped (500 ml/h) onto a SP-Sepharose column (5×15 cm) previously equilibrated with 50 mM HAc at pH=5.0. The column was eluted with a linear gradient between 1500 ml of 50 mM HAc and 1500 ml of 50 mM HAc containing 1.0 M NaCl. Fractions of 10 ml were collected and analysed for the content of CART fragments by analytical HPLC. The chromatogram from the ion exchange chromatography is shown in FIG. 8. Three pools (A, B and C, see FIG. 8) were generated on the basis of the analytical HPLC analysis of the individual fractions. Each of these pools, representing a well defined CART fragment, were further purified by preparative HPLC. The individual pools (120–150 ml) were pumped on a Vydac 214TP1022 (100 ml) reverse phase C4 HPLC column previously equilibrated with 0.1% TFA. The column was washed with 100 ml 0.1% TFA and eluted with a linear gradient from 0 to 70% MeCN in 0.1% TFA at a flow rate of 3 ml/min. The individual fractions from the 3 preparative HPLC purifications were analysed by analytical HPLC and the 3 individual CART fragments were isolated from these fractions by lyophilisation.

Figure 9:
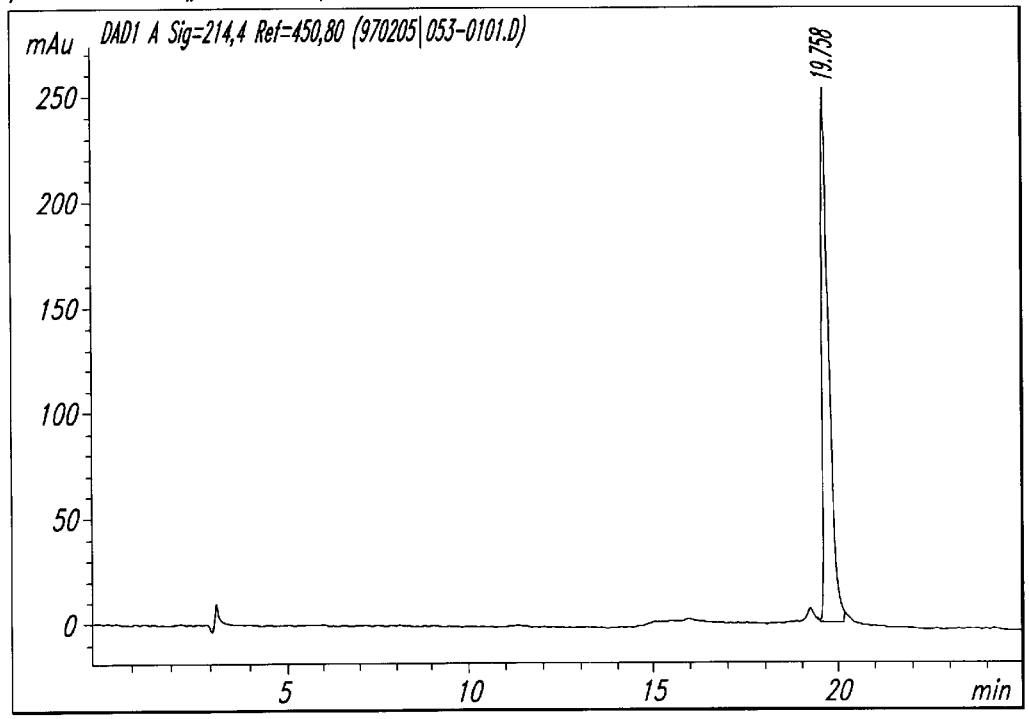
FIG. 9: Analytical HPLC of CART fragment, pool A.
Figure 10:
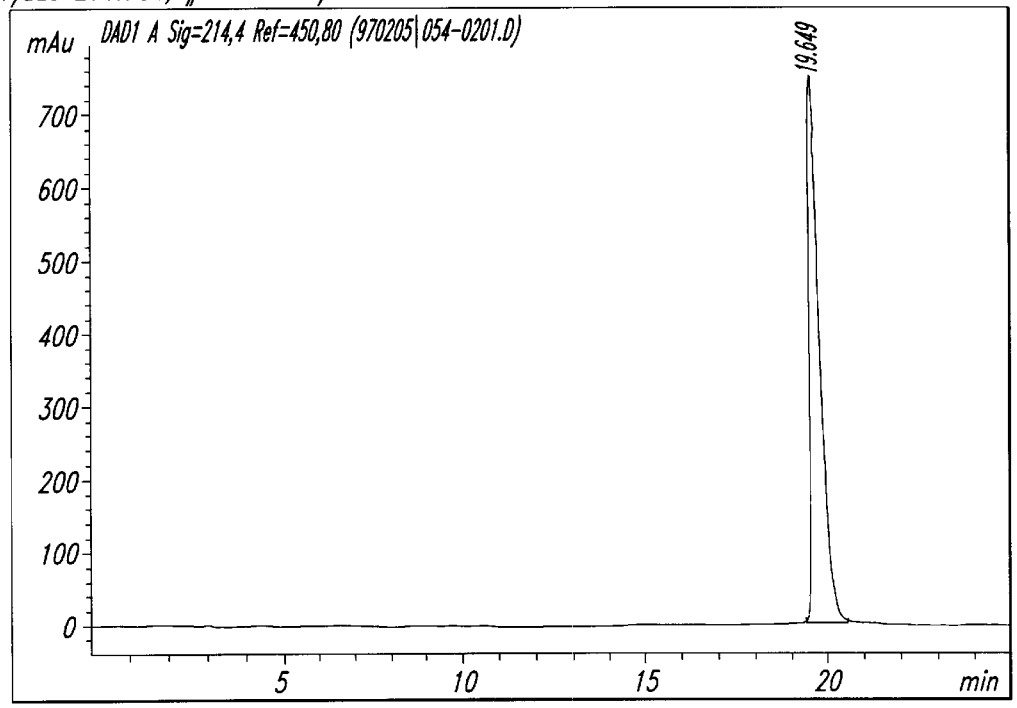
FIG. 10: Analytical HPLC of CART fragment, pool B.
Figure 11:
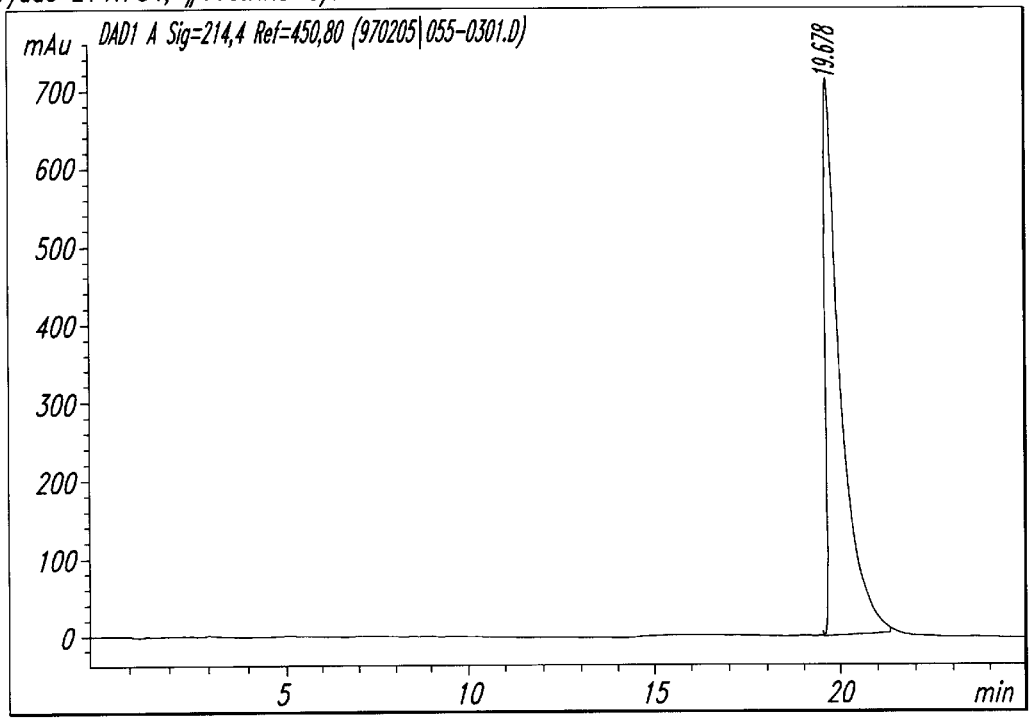
FIG. 11: Analytical HPLC of CART fragment, pool C.

Characterisation of the Isolated CART fragments from the Yeast Fermentation The purity of the 3 isolated CART fragments are shown in FIGS. 9, 10, and 11, respectively. The structure of the 3 purified CART fragments were determined by amino acid sequencing and MALDI-TOF mass spectrometry. The following results were found:

| Pool No. | Sequence found | Mass found | Theoretical mass | Identity |
| --- | --- | --- | --- | --- |
| A | YGQVPM... | 4389.9 | 4387.1 | CART(62-102) |
| B | KYGQVP... | 4516.5 | 4515.3 | CART(61-102) |
| C | RIPIYEKKY... | 5418.0 | 5415.4 | CART(54-102) |

The total yields of the purified rat CART fragments from 4.25 liters of fermentation broth were:

| Pool No. | Identity | Total Yield |
| --- | --- | --- |
| A | CART(62-102) | 33 mg |
| B | CART(61-102) | 200 mg |
| C | CART(54-102) | 280 mg |

CART(62–102) corresponds to SEQ ID No. 8, CART (61–102) corresponds to SEQ ID No. 7 and CART(54–102) corresponds to SEQ ID No. 6.

The human CART(62–102) and CART(61–102) fragments are identical to the rat fragments. Human CART (54–102) differs from the rat fragment by having a valine residue in position 2 in stead of a isoleucine residue. Human CART(54–102) may be prepared using the same method as described for rat CART(54–102) starting from a human tissue or simply by substituting valine for isoleucine in position 2 of rat CART(54–102) according to methods well-known to a person skilled in the art.

Example 8

The Disulphide Bond Configuration in Rat CART (62–102), SEQ ID No. 8

The C-terminal part of the CART molecule contains 6 cysteine residues:
Tyr-Gly-Gln-Val-Pro-Met-Cys-Asp-Ala-Gly-Glu-Gln-Cys-Ala-Val-Arg-Lys-Gly-Ala-Arg-Ile-Gly-Lys-Leu-Cys-Asp-Cys-Pro-Arg-Gly-Thr-Ser-Cys-Asn-Ser-Phe-Leu-Leu-Lys-Cys-Leu In principle these 6 cysteine residues can exist in 5×3×1=15 possible arrangements to form 3 disulphide bonds. The present series of experiments were carried out in order to elucidate, which of the 15 possible arrangements was present in the CART molecule.

The CART fragment (residues 62–102) prepared as described in the preceding example was digested with Armillaria Mellea protease, which cleaves specifically on the N-terminal side of lysine residues. The fragments generated were separated by HPLC and subjected to mass spectrometry and amino acid sequence analyses. From mass spectrometry and sequence analysis it could be deduced that the following two fragments were generated by the Annilaria Mellea protease digestion:
Tyr-Gly-Gln-Val-Pro-Met-Cys-Asp-Ala-Gly-Glu-Gln-Cys-Ala-Val-Arg Lys-Leu-Cys-Asp-Cys-Pro-Arg-Gly-Thr-Ser-Cys-Asn-Ser-Phe-Leu-Leu Lys-Cys-Leu
Lys-Gly-Ala-Arg-Ile-Gly The first of these fragments is a 3 chained molecule still held together by the 3 disulphide bonds. This molecule was subjected to digestion with *Pseudomonas fragi* endoproteinase Asp-N, which cleaves specifically on the N-terminal side of aspartic acid residues. From this digest the following two fragments could be isolated:
Tyr-Gly-Gln-Val-Pro-Met-Cys
Lys-Leu-Cys
Asp-Ala-Gly-Glu-Gln-Cys-Ala-Val-Arg
Asp-Cys-Pro-Arg-Gly-Thr-Ser-Cys-Asn-Ser-Phe-Leu-Leu
Lys-Cys-Leu The first of these fragments is a two chained molecule held together by a single disulphide bond. Thus, cysteine residue I and III of the original molecule must be linked.

The second of these fragments, containing cysteine residue II, IV, V and VI, is a 3 chained molecule linked by 2 disulphide bonds. This molecule was subjected to trypsin digestion and the following two fragments were generated:
Asp-Ala-Gly-Glu-Gln-Cys-Ala-Val-Arg
Gly-Thr-Ser-Cys-Asn-Ser-Phe-Leu-Leu
Asp-Cys-Pro-Arg
Lys-Cys-Leu From these results it is clear that Cys-II and Cys-V are linked and that Cys-IV and Cys-VI are linked.

Figure 12:
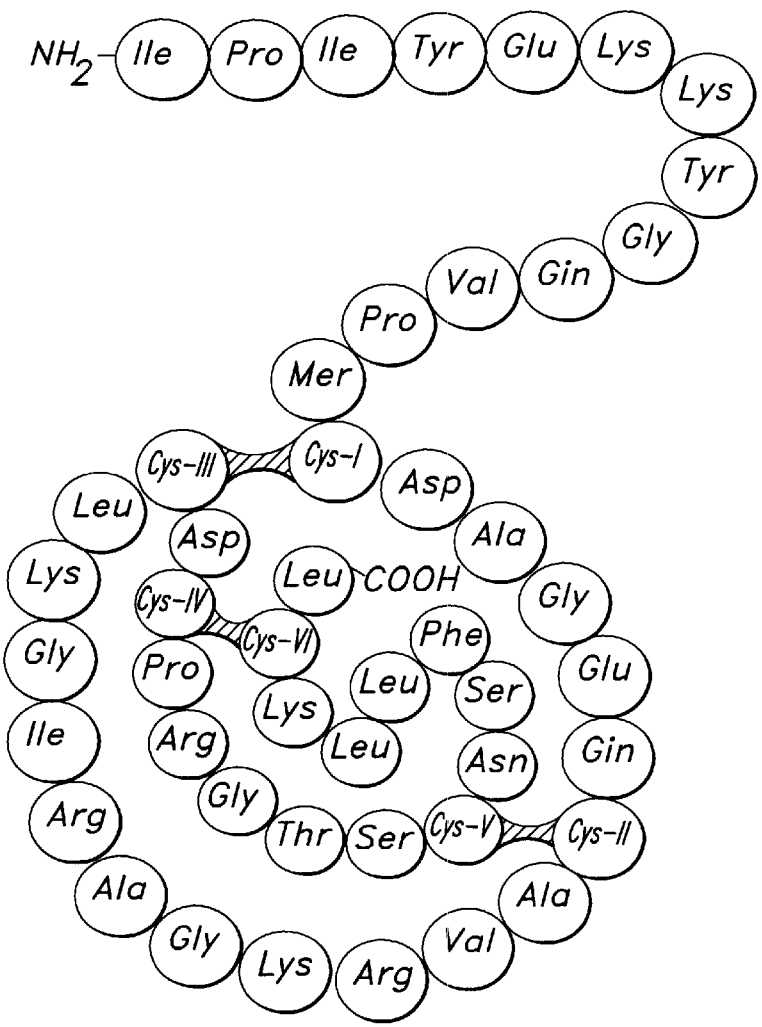
FIG. 12: Primary and secondary structure of "IPI-CART" showing the I–III, II–V and IV–VI disulphide bond configuration.

From the above results the entire primary and secondary structure of the C-terminal part of the CART molecule can be deduced showing that the disulphide bond exists in a I-III, II-V and IV-VI configuration (see FIG. 12).

Example 9

Test Method for Measuring Appetite Suppression in Mice

Mice were deprived of their normal feed for two days and given free access to a solution of nutritionally complete infant formula milk (Complan®) for the first day, after which food deprivation was complete for the last day before testing. After one day of food deprivation, mice were injected intra-cerebroventricularly (ICV) in the lateral ventricle with 10 microliters of a solution containing the test substance. Thirty minutes after injection, mice were individually placed in a 15×15×15 cm test box with a stainless steel grid floor and a glass drinking tube which projected into the box. The drinking tube was connected to a reservoir containing the formula milk solution, and the interior of the drinking tube contained an electrode enabling the detection of drinking contacts with the solution by measuring the flow of a weak (unnoticeable) electric current through mice by means of an electronic apparatus connected to the drinking tube electrode and the stainless steel grid floor. Consumption of the milk solution was measured over a 10 minutes period by electronically recording the total amount of contact with the milk solution during the test session. The degree of appetite suppression produced by a given test substance was determined by statistical comparison of the duration of milk consumption by control (vehicle treated) mice with that of mice treated with a test substance. The degree of appetite suppression in a treated group of mice was expressed as percent reduction of consumption relative to the mean of the control group's response.

Example 10

Test for Appetite Suppression in Mice by Recombinant Rat CART(10–89, Short), SEQ ID No. 10

Mice were tested for appetite suppression as described in Example 9 after treatment with 1–20 micrograms of a test substance consisting of recombinant rat CART(10–89) dissolved in phosphate buffered saline. Intra-cerebroventricular injections of the test substance produced statistically significant suppression of milk consumption.

| Dose (micrograms) | 1 | 2 | 5 | 10 | 20 |
|---|---|---|---|---|---|
| % Feeding Suppression | 41% | 70% | 71% | 59% | 78% |

Example 11

Test for Appetite Suppression in Mice by Recombinant Rat CART(54–102, Long), SEQ ID No. 6

Mice were tested for appetite suppression as described in Example 9 after treatment with 0.5-10 micrograms of a test substance consisting of recombinant rat CART(54–102) dissolved in phosphate buffered saline. Intra-cerebroventricular injections of the test substance produced statistically significant suppression of milk consumption.

| Dose (micrograms) | 0.5 | 1 | 2 | 5 | 10 |
|---|---|---|---|---|---|
| % Feeding Suppression | 13% | 71% | 100% | 100% | 100% |

Example 12

Test for appetite suppression in mice by recombinant rat CART(61–102, long), SEQ ID No. 7

Mice were tested for appetite suppression as described in Example 9 after treatment with 0.5-10 micrograms of a test substance consisting of recombinant rat CART(61–102) dissolved in phosphate buffered saline. Intra-cerebroventricular injections of the test substance produced statistically significant suppression of milk consumption.

| Dose (micrograms) | 0.5 | 1 | 2 | 5 | 10 |
|---|---|---|---|---|---|
| % Feeding Suppression | 74% | 80% | 78% | 100% | 100% |

Example 13

Test for Appetite Suppression in Mice by Recombinant Rat CART(62–102, Long), SEQ ID No. 8

Mice were tested for appetite suppression as described in Example 9 after treatment with 0.5-10 micrograms of a test substance consisting of recombinant rat CART(62–102) dissolved in phosphate buffered saline. Intracerebroventricular injections of the test substance produced statistically significant suppression of milk consumption.

| Dose (micrograms) | 0.5 | 1 | 2 | 5 | 10 |
|---|---|---|---|---|---|
| % Feeding Suppression | 30% | 55% | 60% | 89% | 100% |

Example 14

Effect of Fasting on the Expression of CART mRNA

Rat brain tissue from three different groups of animals (6 animals in each group): normal control, fasted for 48 hours and fasted for 48 hours and re-fed for 3 hours. Cryostat sections were cut and three sections were used for in situ hybridisation with 35-S labelled anti-sense CART RNA. Additional sections were included with a similar amount of 35-S labelled sense RNA probe. Slides were exposed on one Betamax hyperfilm for 7 days. The images were digitized and analysed using the NIH Image software (treatment blinded to the observer). An empirically determined gray level was used to set the threshold on all images after exclusion of those with bad morphology or bad representation of the area in question (indicated by lines on the figure). The average gray scale value of all pixels above this level within the area of interest (PVN or Nucleus Arcuatus (in both the frontal section and at eminentia mediana)) was then measured and multiplied by the size of the area of interest. A mean for each animal was then determined and the standard deviation indicated represents the spreading between animals.

Figure 13:
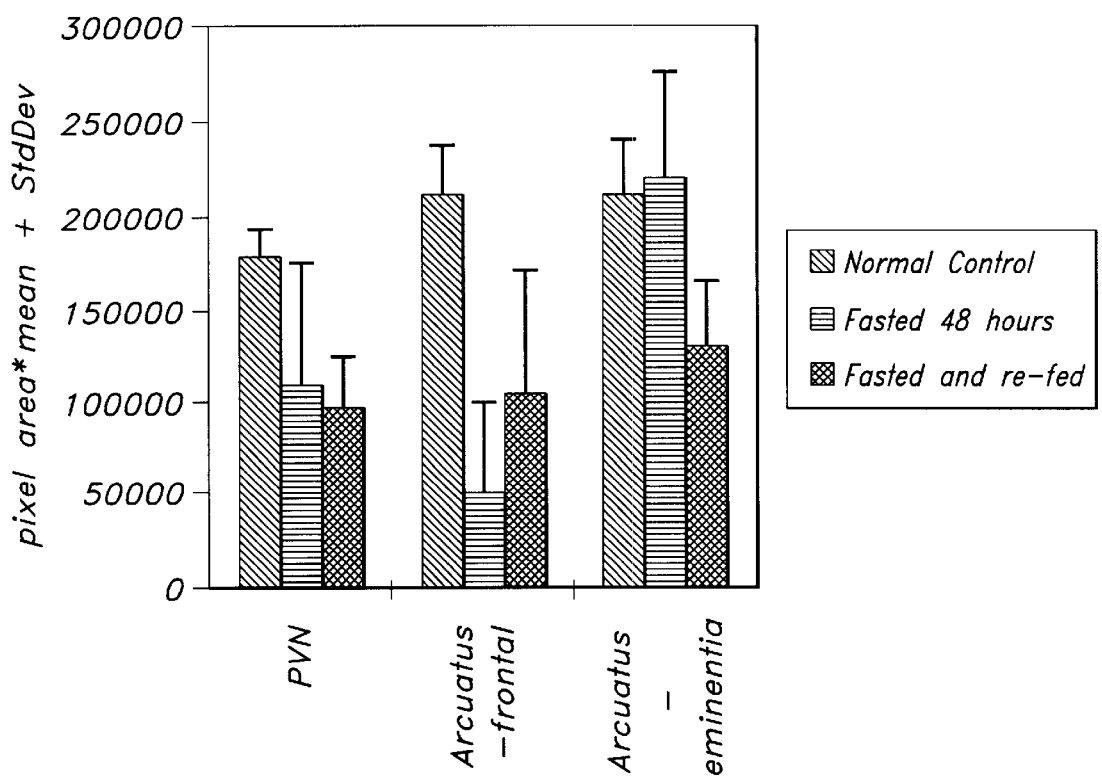
FIG. 13: Effect of fasting on CART mRNA expression.

These results show that CART mRNA is regulated in a manner inverse to that of NPY thus indicating the presence of neurotransmitter mode action for CART involving a receptor mediating a satiety stimulus, presumably along the arcuate-paraventricular nucleus pathway (see FIG. 13).

Example 15

Low Expression of CART mRNA in Arcuate Nucleus of Obese Zucker Rats

Figure 14:
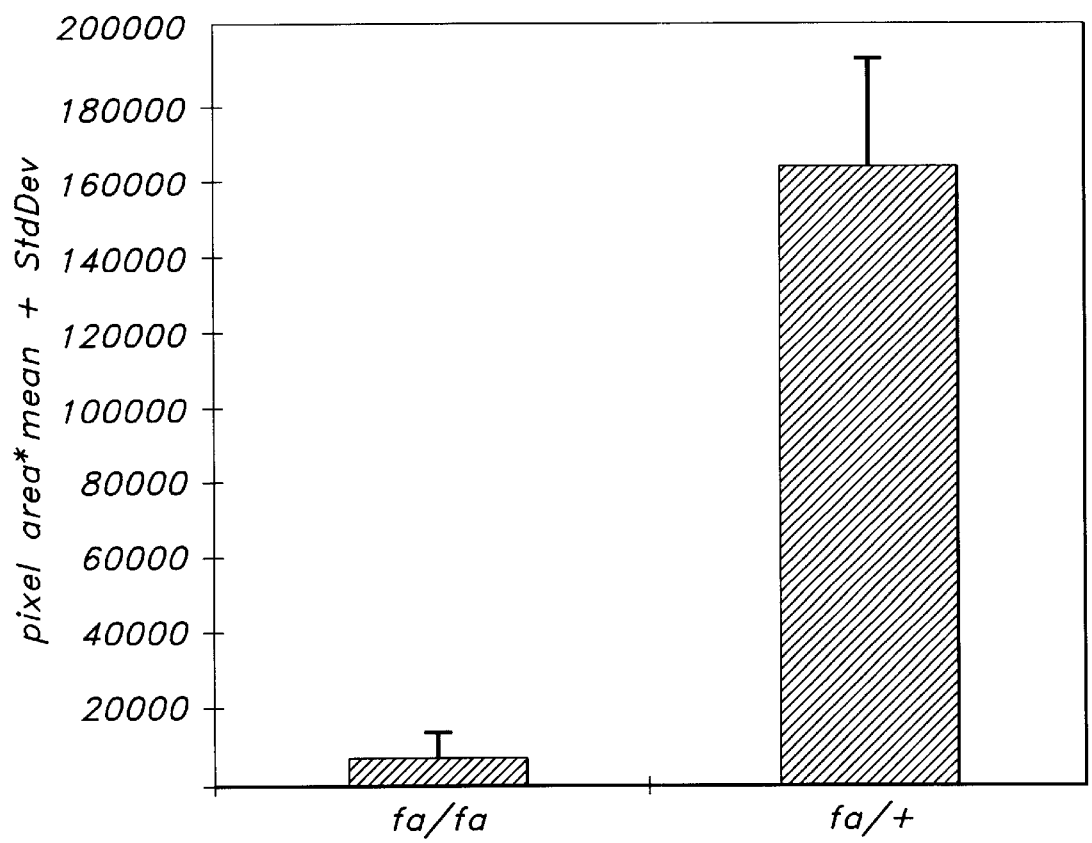
FIG. 14: CART mRNA in Zucker rat arcuate nucleus and heterozygote controls.

Rat brain tissue was obtained from two groups of Zucker rats (6 animals in each group): fa/fa and fa/+. Cryostat sections were cut and three sections were used for in situ hybridisation with 35-S labelled anti-sense CART RNA (rCART5A cDNA (Eco47-HindIII fragment from bp Nos. 226411)). Post-hybridisation washings were performed at 57° C. and 62° C. in 50% formamide. Additional sections were included with a similar amount of 35-S labelled sense RNA probe and these showed no signal. Slides were exposed on one Betamax hyperfilm for 12 days. The images were digitized to 256 grey levels and analysed using the NIH Image software (treatment blinded to the observer). An empirically determined gray level (100) was used to set the threshold on all images after exclusion of those with bad morphology or bad representation of the area in question (three sections) and one set of slides (Nos. 25–27) as one animal due to an error was represented twice (and one missing). The average gray scale value of all pixels above the arcuate nucleus was then measured. A mean for each animal was then determined and the product of the area and mean calculated. These results show that CART mRNA is regulated in a manner inverse to that of NPY thus indicating the presence of neurotransmitter mode action for CART involving a receptor mediating a satiety stimulus, presumably along the arcuate-paraventricular nucleus pathway. Furthermore, the strong decrease in CART expression in the obese Zucker rat deficient in leptin signalling strongly implicates CART mediated neuronal signalling in a satiety mediating pathway in the hypothalamus (see FIG. 14).

Example 16

Preparation of Rat CART(55–102), SEQ ID No. 4

Figure 15:
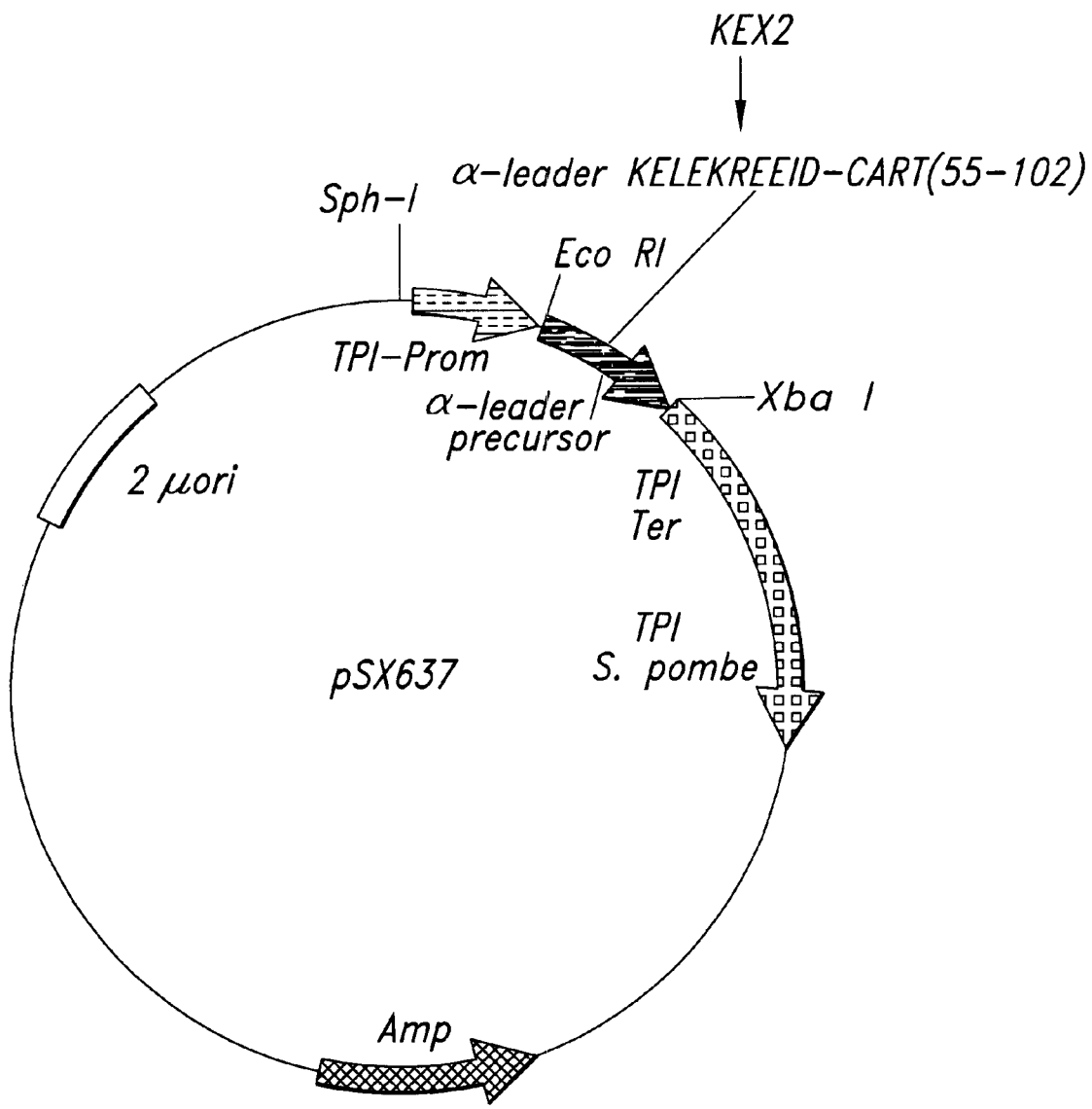
FIG. 15: *S. cerevisiae* plasmid for the expression and secretion of Glu-Glu-Ile-Asp-CART(55–102). TPI-prom. and TPI-term. are *S. cerevisiae* triosephosphate isomerase transcription promoter and terminator sequences, respectively. TPI S. pombe is the *Schizosaccharmyces pombe* triosephosphate isomerase gene. Only restriction sites relevant for the plasmid construction have been indicated.

Plasmid pSX637, encoding Glu-Glu-Ile-Asp-CART (55–102), was constructed by the use of the PCR technique "Splicing by Overlap Extension" (Horton et al., Gene 77:61–68, 1989) and the product was inserted into pAK405 (Example 5). The resulting expression plasmid (pSX637) is shown in FIG. 15. As can be seen from this figure a sequence of: Lys-Glu-Leu-Glu has been placed between the α-leader and Kex2 site in order to optimise processing (Kjeldsen et al., Gene 170:107–112, 1996).

Plasmid pSX637 was transformed into *Saccharomyces. cerevisiae* strains ME1487 (MATαΔyap3::URA3 Δtpi:.LEU2 pep4–3 Δura3 leu2) and ME1719 (MATα/MATαΔyap3::URA3 /Δyap3::URA3 Δtpi:.LEU2/Δtpi::LEU2 pep4–3/pep4–3 Δura3/Δura3 hleu2/leu2), respectively. Host cells were cultured in YPGGE medium (1% (w/v) yeast extract, 2% (w/v) peptone, 2% (w/v) galactose, 2% (v/v) glycerol and 1% (v/v) ethanol) to $OD_{600}$ nm of 0.2. Transformation was made by using a standard protoplast method. Transformant YES1789, was obtained containing the EEID-CART expressing plasmid after transformants were selected on minimal plates containing glucose.

Fermentation of EEID-CART(55–102) (yeast strain: YES1789) was carried out in 6 L stainless steel fermentor from Chemap A/B, Switzerland equipped with bottom stirrer and in situ steam sterilization. The medium was composed essentially as previously described (Thim et al., FEBS Lett. 318:345–352, 1993) and a starting volume of 4.0 L was chosen. Ammonia was added to adjust pH throughout the fermentation to 4.9 and the temperature was kept constant at 30° C. with steam/cooling water. Dissolved oxygen was kept above 50% saturation by frequent adjustment of the stirrer speed. The inoculum was from a YPD (Yeast-extract Peptone Dextrose) culture (2 days, 30° C.). Glucose (1250 g) was dissolved in water to a volume of 2 L, sterilised separately in an autoclave (30 min, 121° C.), and added with a constant rate of 30 g/h over the first 24 hours. The rate was increased to 60 g/h over the next 24 hours. After 48 hours of cultivation the broth was harvested. The EEID-CART (55–102) broth was adjusted to pH 11 with 3 N NaOH and kept at 25° C. for 30 min before centrifugation as above. The supernatant was adjusted to pH 9.7 to protect against proteolysis before the purification was initiated. The dry biomass in the two fermentations was 73.6 g/L. The weight of the total fermentation broth was 5706 g. The fermentation supernatant (4.6 L) from yeast strain YES1789 expressing Glu-Glu-Ile-Asp-CART(55–102) was dialysed against 60 L of water at 4° C. for 96 h. The pH was adjusted to 4.3 and the solution was pumped onto a SP-Sepharose (Pharmacia) column (5×15 cm) with a flow rate of 300 mL/h. Prior to the application the column was equilibrated with 50 mM HAc buffer pH 4.25. The column was washed with 3 L of 50 mM HAc buffer pH 4.25. EEID-CART(55–102) was eluted from the column by a linear gradient between 1.5 L of 50 mM HAc buffer pH 4.25 and 1.5 L of 50 mM HAc buffer pH 4.25 containing 1M NaCl. Fractions (10 mL) were collected at a flow rate of 100 mL/h and the absorbance was measured at 280 nm. The EEID-CART(55–102) molecule eluted at 0.5M of NaCl and fractions containing the peptide were dialysed against 25 L of 50 mM HAc buffer pH 4.5 at 4° C. for 96 h. L-Cystein was added to the solution (560 mL) to give a final concentration of 1 mM, and 4.5 mL dipeptidylaminopeptidase-1 (DAP-1, Cathepsin C from chicken liver, EC 3.4.14.1, Unizyme Laboratories) was added. The resulting concentration of DAP-1 was 20 units/mL. The digestion of EEID-CART(55–102) was carried out at 37° C. and aliquots were analysed by HPLC each half hour. After incubation for 4.5 h more than 98% of the precursor was converted to CART(55–102). The digestion mixture was adjusted to pH 4.25 and pumped (60 mL/h) onto a SP-Sepharose (Pharmacia) column (5×8 cm) previously equilibrated with 50 mM HAc buffer pH 4.25. The column was washed with 1.6 L of equilibration buffer and CART(55–102) was eluted with a linear gradient between 1 L of 50 mM HAc buffer pH 4.25 and 1 L of 50 mM HAc buffer pH 4.25 containing 1.2 M NaCl, at a flow rate of 100 mL/h. The absorbance at 280 nm was recorded and fractions of 10 mL were collected. The CART(55–102) molecule eluted at 0.67 M of NaCl and fractions containing the peptide were pooled. The solution was divided into 5 equal portions. Each portion was pumped on a Vydac 214TP1022 reverse phase C4 preparative HPLC column (2.2×25 cm) previously equilibrated with 0.1% (v/v) TFA. The column was washed with 100 mL 0.1% (v/v) TFA and eluted with a linear gradient from 0 to 70% (v/v) acetonitrile in 0.1% (v/v) TFA at a flow rate of 3 mL/min. The CART(55–102) containing fractions from the 5 preparative HPLC purifications were pooled and the peptide was isolated from these fractions by lyophilisation. The total yield of CART (55–102) from 4.6 L of fermentation supernatant was 705 mg.

N-terminal amino acid sequences were determined by automated Edman degradations using an Applied Biosystem Model 494 Protein Sequencer essentially as described by the manufacturer. The N-terminal sequence of the purified CART(55–102) was found to be: IPIYEKKYGQ . . .

Mass spectrometric analysis on the isolated CART (55–102) was performed on a Voyager RP MALDI-TOF instrument (Perseptive Biosystems Inc., Framingham, Mass.) equipped with a nitrogen laser (337 nm). The instrument was operated in linear mode with delayed extraction, and the accelerating voltage in the ion source was 25 kV.

Sample preparation was done as follows: 1 µL sample solution was mixed with 10 µL matrix solution (alpha-cyano-4-hydroxy-cinnamic acid dissolved in a 5:4:1 (v/v/v) mixture of acetonitrile: water: 3% (v/v) TFA) and 1 µL was deposited on the sample plate and allowed to dry. Calibration was performed using external standards and the accuracy of the mass determinations is within 0.1%. The mass found for the isolated CART(55–102) was 5257.1 as compared to a calculated mass of 5255.5.

Example 17

Test for Appetite Suppression in Mice by Recombinant Rat CART(55–102. Long), SEQ ID No. 4

Mice were tested for appetite suppression as described in Example 9 after treatment with 0.1–1.0 micrograms of a test substance consisting of recombinant CART(55–102) dissolved in phosphate buffered saline. Intra-cerebroventricular injections of the test substance produced a statistically significant suppression of milk consumption.

| Dose (micrograms) | 0.1 | 0.2 | 0.5 | 1.0 |
|---|---|---|---|---|
| % Feeding Suppression | 38% | 61% | 98% | 99% |

The human CART(55–102) peptide corresponding to SEQ ID No. 5 differs from the rat form by having a valine residue in stead of a isoleucine residue in position 1. It may be prepared using the same method as described for the rat form starting from a human tissue or simply by substituting valine for isoleucine in position 1 of the rat form.

Example 18

Test for Appetite Suppression in Mice by Fragmented Recombinant Rat CART(55–102 Long) . SEQ ID No. 4

Mice were tested for appetite suppression as described in Example 9 after treatment with 0.1-2.0 µg of a test substance consisting of fragmented recombinant rat CART(55–102) (fragmented by trypsin and endopeptidase Asp-N) dissolved in phosphate buffered saline. Intra-cerebroventricular injections of the test substance did not produce statistically significant suppression of milk consumption at any dose tested (see table).

| Dose (micrograms) | 0.1 | 0.2 | 0.5 | 1 | 2 |
|---|---|---|---|---|---|
| % Feeding Suppression | 1% | 0% | 3% | 0% | 0% |

Example 19

Test for Appetite Suppression in Mice by Recombinant Rat CART(55–102 Long), SEQ ID No. 4 with a Disrupted Secondary Structure Mice were tested for appetite suppression as described in Example 9 after treatment with 0.1–2.0 µg of a test substance consisting of recombinant rat CART(55–102) with a disrupted secondary structure (reduced and pyridylated) dissolved in phosphate buffered saline. Intra-cerebroventricular injections of the test substance did not produce statistically significant suppression of milk consumption at any dose tested (see table).

| Dose (micrograms) | 0.1 | 0.2 | 0.5 | 1 | 2 |
|---|---|---|---|---|---|
| % Feeding Suppression | 9% | 12% | 0% | 26% | 18% |

Example 20

Test Method for Measuring Appetite Suppression after Intra-cerebral Injection of a Test Substance in Rats Male Wistar rats were implanted with a guide cannula in the lateral cerebral ventricle and allowed to recover for 4–8 days before screening for functional cannulae. This was accomplished by injection of 5 µg of porcine neuropeptide Y (NPY), which stimulates feeding with intra-cerebral administration. Animals not responding to NPY were discarded, and the remaining rats were sorted into response-equivalent groups of 5–6 rats each. To test the appetite suppressing effects of compounds, the rats were first food deprived for 24 hours and then received a 5 μl intra-cerebroventricular injection of a test substance dissolved in phosphate buffered saline (PBS). A control group injected with 5 μl of PBS provided reference data for each experiment. Consumption of a special test food (a mash made from a 2:1 mixture of water and dry standard chow) was measured for one hour following the injection. The degree of appetite suppression produced by a given test substance was determined by statistical comparison of the amount of food consumed by control rats (vehicle treated) with that of rats treated with a test substance. The degree of feeding suppression in a group of rats was expressed as percent reduction of consumption relative to the mean amount consumed by the control group.

Example 21

Test for Appetite Suppression in Rats by
Recombinant Rat CART(55–102, Long), SEQ ID
No. 4

Rats were tested for appetite suppression as described in Example 20 after treatment with 1 μg of a test substance consisting of recombinant rat CART(55–102) dissolved in phosphate buffered saline. Intra-cerebroventricular injection of 1μ of the test substance produced a statistically significant 52% suppression of food consumption.

Example 22

Test for Appetite Suppression in Rats by
Recombinant Rat CART(55–102, Long), SEQ ID
No. 4

Rats were tested for appetite suppression as described in Example 20 after treatment with 0.1-3.0 μg of a test substance consisting of recombinant rat CART(55–102) dissolved in phosphate buffered saline. Intra-cerebroventricular injection of 0.3 μg and 3.0 μg of the test substance produced statistically significant suppression of food consumption (see table).

| Dose (micrograms)     | 0.1 | 0.3 | 1   | 3   |
|-----------------------|-----|-----|-----|-----|
| % Feeding Suppression | 17% | 45% | 19% | 63% |

What is claimed is:

1. An isolated polypeptide consisting of the sequence set forth in SEQ ID NO: 4:
Ile-Pro-Ile-Tyr-Glu-Lys-Tyr-Gly-Gln-Val-Pro-Met-Cys-Asp-Ala-Gly-Glu-Gln-Cys- Ala-Val-Arg-Lys-Gly-Ala-Arg-Ile-Gly-Lys-Leu-Cys-Asp-Cys-Pro-Arg-Gly-Thr-Ser- Cys-Asn-Ser-Phe-Leu-Lys-Cys-Leu, wherein said polypeptide has appetite suppressing activity.

2. Am isolated peptide according to claim 1, wherein the cysteine residues are linked by disulphide bonds in the configuration I–III, II–V and IV–VI when the cysteines are numbered I–VI consecutively from the N-terminal end.

3. An isolated polypeptide consisting of the sequence set forth in SEQ ID NO:5:
Val-Pro-Ile-Tyr-Glu-Lys-Lys-Tyr-Gly-Gln-Val-Pro-Met-Cys-Asp-Ala-Gly-Glu-Gln- Cys-Ala-Val-Arg-Lys-Gly-Ala-Arg-Ile-Gly-Lys-Leu-Cys-Asp-Cys-Pro-Arg-Gly-Thr- Ser-Cys-Asn-Ser-Phe-Leu-Leu-Lys-Cys-Leu, wherein said polypeptide has appetite supressing activity.

4. An isolated polypeptide according to claim 3, wherein the cysteine residues are linked by disulphide bonds in the configuration I–III, II–V and IV–VI when the cysteines are numbered I–VI consecutively from the N-terminal end.

5. An isolated polypeptide consisting of the sequence set forth in SEQ ID NO: 6:
Arg-Ile-Pro-Ile-Tyr-Glu-Lys-Lys-Tyr-Gly-Gln-Val-Pro-Met-Cys-Asp-Ala-Gly-Glu-Gln- Cys-Ala-Val-Arg-Lys-Gly-Ala-Arg-Ile-Gly-Lys-Leu-Cys-Asp-Cys-Pro-Arg-Gly-Thr- Ser-Cys-Asn-Ser-Phe-Leu-Leu-Lys-Cys-Leu, wherein said polypeptide has appetite suppressing activity.

6. An isolated polypeptide according to claim 5 wherein the cysteine residues are linked by disulphide bonds in the configuration I–III, II–V and IV–VI when the cysteines are numbered I–VI consecutively from the N-terminal end.

7. An isolated polypeptide consisting of the sequence set forth in SEQ ID NO: 7:
Lys-Tyr-Gly-Gln-Val-Pro-Met-Cys-Asp-Ala-Gly-Glu-Gln-Cys-Ala-Val-Arg-Lys-Gly- Ala-Arg-Ile-Gly-Lys-Leu-Cys-Asp-Cys-Pro-Arg-Gly-Thr-Ser-Cys-Asn-Ser-Phe-Leu- Leu-Lys-Cys-Leu, wherein said polypeptide has appetite suppresing activity.

8. An isolated polypeptide according to claim 1, wherein the cysteine residues are linked by disulphide bonds in the configuration I–III, II–V and IV–VI when the cysteines are numbered I–VI consecutively from the N-terminal end.

9. An isolated polypeptide consisting of the sequence set forth in SEQ ID NO: 8:
Tyr-Gly-Gln-Val-Pro-Met-Cys-Asp-Ala-Gly-Glu-Gln-Cys-Ala-Val-Arg-Lys-Gly-Ala- Arg-Ile-Gly-Lys-Leu-Cys-Asp-Cys-Pro-Arg-Gly-Thr-Ser-Cys-Asn-Ser-Phe-Leu-Leu- Lys-Cys-Leu, wherein said polypeptide has appetite suppressing activity.

10. An isolated polypeptide according to claim 9, wherein the cysteine residues are linked by disulphide bonds in the configuration I–III, II–V and IV–VI when the cysteines are numbered I–VI consecutively from the N-terminal end.

11. An isolated polypeptide consisting of the sequence set forth in SEQ ID NO: 9:
Cys-Asp-Ala-Gly-Glu-Gln-Cys-Ala-Val-Arg-Lys-Gly-Ala-Arg-Ile-Gly-Lys-Leu-Cys- Asp-Cys-Pro-Arg-Gly-Thr-Ser-Cys-Asn-Ser-Phe-Leu-Leu-Lys-Cys-Leu, wherein said polypeptide has appetite suppressing activity.

12. An isolated polypeptide according to claim 11, wherein the cysteine residues are linked by disulphide bonds in the configuration I–III, II–V and IV–VI when the cysteines are numbered I–VI consecutively from the N-terminal end.

13. An appetite suppresing composition comprising:
(i) a polypeptide having appetite-regulating activity selected from the group consisting of SEQ ID NOS: 4–9 and
(ii) a pharmaceutically acceptable carrier.

14. An appetite regulating composition according to claim 13 4–9 wherein the cysteine residues in said polypeptide are linked by disulfide bonds in the configuration I–III, II–V and IV–VI when the cysteines are numbered I–VI consecutively from the N-terminal end.

* * * * *